US011299494B2

United States Patent
Weinstein et al.

(10) Patent No.: US 11,299,494 B2
(45) Date of Patent: Apr. 12, 2022

(54) SUBSTITUTED IMIDAZO[1,2-B]PYRIDAZINES AS INTERLEUKIN-23 AND INTERFERON-α MODULATORS

(71) Applicant: BRISTOL-MYERS SQUIBB COMPANY, Princeton, NJ (US)

(72) Inventors: David S. Weinstein, San Diego, CA (US); John V. Duncia, Newtown, PA (US); Steven H. Spergel, Warrington, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 412 days.

(21) Appl. No.: 16/461,479

(22) PCT Filed: Nov. 16, 2017

(86) PCT No.: PCT/US2017/061895
§ 371 (c)(1),
(2) Date: May 16, 2019

(87) PCT Pub. No.: WO2018/093968
PCT Pub. Date: May 24, 2018

(65) Prior Publication Data
US 2021/0323966 A1 Oct. 21, 2021

Related U.S. Application Data

(60) Provisional application No. 62/423,409, filed on Nov. 17, 2016.

(51) Int. Cl.
*A61K 31/5025* (2006.01)
*C07D 487/04* (2006.01)
*C07D 519/00* (2006.01)

(52) U.S. Cl.
CPC ......... *C07D 487/04* (2013.01); *C07D 519/00* (2013.01)

(58) Field of Classification Search
CPC ............................. A61K 31/5025; C07D 487/04
USPC .......................................... 514/248; 544/236
See application file for complete search history.

(56) References Cited

U.S. PATENT DOCUMENTS 10,479,793 B2 * 11/2019 Weinstein ............... A61P 37/02

FOREIGN PATENT DOCUMENTS

WO WO2009100375 A1 8/2009
WO WO2017087590 A1 5/2017

OTHER PUBLICATIONS

Jordan, V. C. Nature Reviews: Drug Discovery, 2, 2003, 205.*
Hackam, et al. JAMA, 296(14), 2006, 1731-1732.*
U.S. Appl. No. 15/102,991, filed Jun. 9, 2016, Granted (10273237).
PCT/US2014/069476, Dec. 10, 2014, Published (WO2015/089143).
U.S. Appl. No. 16/339,744, filed Apr. 5, 2019, Filed.
PCT/US2017/054710, Oct. 2, 2017, Published (WO2018/067432).
U.S. Appl. No. 15/776,094, filed May 15, 2018, Filed.
PCT/US2016/062396, Nov. 17, 2016, Published (WO2017/087590).

* cited by examiner

*Primary Examiner* — Douglas M Willis
(74) *Attorney, Agent, or Firm* — Elliott Korsen

(57) ABSTRACT

Compounds of formula (I) or a stereoisomer or pharmaceutically-acceptable salt thereof, are useful in the modulation of IL-12, IL-23 and/or IFNα, by acting on Tyk-2 to cause signal transduction inhibition.

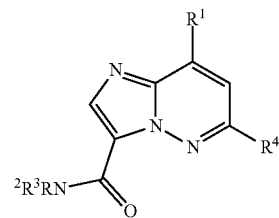

formula (I)

20 Claims, No Drawings
Specification includes a Sequence Listing.

SUBSTITUTED IMIDAZO[1,2-B]PYRIDAZINES AS INTERLEUKIN-23 AND INTERFERON-α MODULATORS

CROSS-REFERENCE TO RELATED APPLICATIONS

This application claims the benefit of U.S. Provisional Application No. 62/423,409 filed Nov. 17, 2016, the disclosure of which is incorporated herein by reference in its entirety.

FIELD OF THE INVENTION

This invention relates to compounds useful in the modulation of IL-12, IL-23 and/or IFNα by acting on Tyk-2 to cause signal transduction inhibition. Provided herein are imidazopyradazine compounds, compositions comprising such compounds, and methods of their use. The invention further pertains to pharmaceutical compositions containing at least one compound according to the invention that are useful for the treatment of conditions related to the modulation of IL-12, IL-23 and/or IFNα in a mammal.

BACKGROUND OF THE INVENTION

The heterodimeric cytokines interleukin IL-12 and IL-23, which share a common p40 subunit, are produced by activated antigen-presenting cells and are critical in the differentiation and proliferation of Th1 and Th17 cells, two effector T cell lineages which play key roles in autoimmunity. IL-23 is composed of the p40 subunit along with a unique p19 subunit. IL-23, acting through a heterodimeric receptor composed of IL-23R and IL-12Rβ1, is essential for the survival and expansion of Th17 cells which produce pro-inflammatory cytokines such as IL-17A, IL-17F, IL-6 and TNF-α (McGeachy, M. J. et al., "The link between IL-23 and Th17 cell-mediated immune pathologies", Semin. Immunol., 19:372-376 (2007)). These cytokines are critical in mediating the pathobiology of a number of autoimmune diseases, including rheumatoid arthritis, multiple sclerosis, inflammatory bowel disease, and lupus. IL-12, in addition to the p40 subunit in common with IL-23, contains a p35 subunit and acts through a heterodimeric receptor composed of IL-12Rβ1 and IL-12Rβ2. IL-12 is essential for Th1 cell development and secretion of IFNγ, a cytokine which plays a critical role in immunity by stimulating MHC expression, class switching of B cells to IgG subclasses, and the activation of macrophages (Gracie, J. A. et al., "Interleukin-12 induces interferon-gamma-dependent switching of IgG alloantibody subclass", Eur. J. Immunol., 26:1217-1221 (1996); Schroder, K. et al., "Interferon-gamma: an overview of signals, mechanisms and functions", J. Leukoc. Biol., 75(2):163-189 (2004)).

The importance of the p40-containing cytokines in autoimmunity is demonstrated by the discovery that mice deficient in either p40, p19, or IL-23R are protected from disease in models of multiple sclerosis, rheumatoid arthritis, inflammatory bowel disease, lupus and psoriasis, among others (Kyttaris, V. C. et al., "Cutting edge: IL-23 receptor deficiency prevents the development of lupus nephritis in C57BL/6-lpr/lpr mice", J. Immunol., 184:4605-4609 (2010); Hong, K. et al., "IL-12, independently of IFN-gamma, plays a crucial role in the pathogenesis of a murine psoriasis like skin disorder", J. Immunol., 162:7480-7491 (1999); Hue, S. et al., "Interleukin-23 drives innate and T cell-mediated intestinal inflammation", J. Exp. Med., 203:2473-2483 (2006); Cua, D. J. et al., "Interleukin-23 rather than interleukin-12 is the critical cytokine for autoimmune inflammation of the brain", Nature, 421:744-748 (2003); Murphy, C. A. et al., "Divergent pro- and anti-inflammatory roles for IL-23 and IL-12 in joint autoimmune inflammation", J. Exp. Med., 198:1951-1957 (2003)).

In human disease, high expression of p40 and p19 has been measured in psoriatic lesions, and Th17 cells have been identified in active lesions in the brain from MS patients and in the gut mucosa of patients with active Crohn's disease (Lee, E. et al., "Increased expression of interleukin 23 p19 and p40 in lesional skin of patients with psoriasis vulgaris", J. Exp. Med., 199:125-130 (2004); Tzartos, J. S. et al., "Interleukin-17 production in central nervous system infiltrating T cells and glial cells is associated with active disease in multiple sclerosis", Am. J. Pathol., 172:146-155 (2008)). The mRNA levels of p19, p40, and p35 in active SLE patients were also shown to be significantly higher compared with those in inactive SLE patients (Huang, X. et al., "Dysregulated expression of interleukin-23 and interleukin-12 subunits in systemic lupus erythematosus patients", Mod. Rheumatol., 17:220-223 (2007)), and T cells from lupus patients have a predominant Th1 phenotype (Tucci, M. et al., "Overexpression of interleukin-12 and T helper 1 predominance in lupus nephritis", Clin. Exp. Immunol., 154:247-254 (2008)).

Moreover, genome-wide association studies have identified a number of loci associated with chronic inflammatory and autoimmune diseases that encode factors that function in the IL-23 and IL-12 pathways. These genes include IL23A, IL12A, IL12B, IL12RB1, IL12RB2, IL23R, JAK2, TYK2, STAT3, and STAT4 (Lees, C. W. et al., "New IBD genetics: common pathways with other diseases", Gut, 60:1739-1753 (2011); Tao, J. H. et al., "Meta-analysis of TYK2 gene polymorphisms association with susceptibility to autoimmune and inflammatory diseases", Mol. Biol. Rep., 38:4663-4672 (2011); Cho, J. H. et al., "Recent insights into the genetics of inflammatory bowel disease", Gastroenterology, 140:1704-1712 (2011)).

Indeed, anti-p40 treatment, which inhibits both IL-12 and IL-23, as well as IL-23-specific anti-p19 therapies have been shown to be efficacious in the treatment of autoimmunity in diseases including psoriasis, Crohn's Disease and psoriatic arthritis (Leonardi, C. L. et al., "PHOENIX 1 study investigators. Efficacy and safety of ustekinumab, a human interleukin-12/23 monoclonal antibody, in patients with psoriasis: 76-week results from a randomized, double-blind, placebo-controlled trial (PHOENIX 1)", Lancet, 371:1665-1674 (2008); Sandborn, W. J. et al., "Ustekinumab Crohn's Disease Study Group. A randomized trial of Ustekinumab, a human interleukin-12/23 monoclonal antibody, in patients with moderate-to-severe Crohn's disease", Gastroenterology, 135:1130-1141 (2008); Gottlieb, A. et al., "Ustekinumab, a human interleukin 12/23 monoclonal antibody, for psoriatic arthritis: randomized, double-blind, placebo-controlled, crossover trial", Lancet, 373:633-640 (2009)). Therefore, agents which inhibit the action of IL-12 and IL-23 may be expected to have therapeutic benefit in human autoimmune disorders.

The Type I group of interferons (IFNs), which include the IFNα members as well as IFNβ, IFNε, IFNκ and IFNω, act through a heterodimer IFNα/β receptor (IFNAR). Type I IFNs have multiple effects in both the innate and adaptive immune systems including activation of both the cellular and humoral immune responses as well as enhancing the expression and release of autoantigens (Hall, J. C. et al., "Type I interferons: crucial participants in disease amplification in autoimmunity", *Nat. Rev. Rheumatol.*, 6:40-49 (2010)).

In patients with systemic lupus erythematosus (SLE), a potentially fatal autoimmune disease, increased serum levels of interferon (IFN)-α (a type I interferon) or increased expression of type I IFN-regulated genes (a so-called IFNα signature) in peripheral blood mononuclear cells and in affected organs has been demonstrated in a majority of patients (Bennett, L. et al., "Interferon and granulopoiesis signatures in systemic lupus erythematosus blood", *J. Exp. Med.*, 197:711-723 (2003); Peterson, K. S. et al., "Characterization of heterogeneity in the molecular pathogenesis of lupus nephritis from transcriptional profiles of laser-captured glomeruli", *J. Clin. Invest.*, 113:1722-1733 (2004)), and several studies have shown that serum IFNα levels correlate with both disease activity and severity (Bengtsson, A. A. et al., "Activation of type I interferon system in systemic lupus erythematosus correlates with disease activity but not with antiretroviral antibodies", *Lupus*, 9:664-671 (2000)). A direct role for IFNα in the pathobiology of lupus is evidenced by the observation that the administration of IFNα to patients with malignant or viral diseases can induce a lupus-like syndrome. Moreover, the deletion of the IFNAR in lupus-prone mice provides high protection from autoimmunity, disease severity and mortality (Santiago-Raber, M. L. et al., "Type-I interferon receptor deficiency reduces lupus-like disease in NZB mice", *J. Exp. Med.*, 197:777-788 (2003)), and genome-wide association studies have identified loci associated with lupus that encode factors that function in the type I interferon pathway, including IRF5, IKBKE, TYK2, and STAT4 (Deng, Y. et al., "Genetic susceptibility to systemic lupus erythematosus in the genomic era", *Nat. Rev. Rheumatol.*, 6:683-692 (2010); Sandling, J. K. et al., "A candidate gene study of the type I interferon pathway implicates IKBKE and IL8 as risk loci for SLE", *Eur. J. Hum. Genet.*, 19:479-484 (2011)). An antibody directed against the Type-I interfereon receptor has been reported to provide benefits to lupus patients (Furie R, et al, "Anifrolumab, an Anti-Interferon Alpha Receptor Monoclonal Antibody, in Moderate to Severe Systemic Lupus Erythematosus (SLE)", [abstract] *Arthritis Rheumatol.* 2015; 67 (suppl 10)). In addition to lupus, there is evidence that aberrant activation of type I interferon-mediated pathways are important in the pathobiology of other autoimmune diseases such as Sjögren's syndrome and scleroderma (Bäve, U. et al., "Activation of the type I interferon system in primary Sjögren's syndrome: a possible etiopathogenic mechanism", *Arthritis Rheum.*, 52:1185-1195 (2005); Kim, D. et al., "Induction of interferon-alpha by scleroderma sera containing autoantibodies to topoisomerase I: association of higher interferon-alpha activity with lung fibrosis", *Arthritis Rheum.*, 58:2163-2173 (2008)). Therefore, agents which inhibit the action of type I interferon responses may be expected to have therapeutic benefit in human autoimmune disorders.

Tyrosine kinase 2 (Tyk2) is a member of the Janus kinase (JAK) family of nonreceptor tyrosine kinases and has been shown to be critical in regulating the signal transduction cascade downstream of receptors for IL-12, IL-23 and type I interferons in both mice (Ishizaki, M. et al., "Involvement of Tyrosine Kinase-2 in Both the IL-12/Th1 and IL-23/Th17 Axes In Vivo" *J. Immunol.*, 187:181-189 (2011); Prchal-Murphy, M. et al., "TYK2 kinase activity is required for functional type I interferon responses in vivo" *PLoS One*, 7:e39141 (2012)) and humans (Minegishi, Y. et al., "Human tyrosine kinase 2 deficiency reveals its requisite roles in multiple cytokine signals involved in innate and acquired immunity" *Immunity*, 25:745-755 (2006)). Tyk2 mediates the receptor-induced phosphorylation of members of the STAT family of transcription factors, an essential signal that leads to the dimerization of STAT proteins and the transcription of STAT-dependent pro-inflammatory genes. Tyk2-deficient mice are resistant to experimental models of colitis, psoriasis and multiple sclerosis, demonstrating the importance of Tyk2-mediated signaling in autoimmunity and related disorders (Ishizaki, M. et al., "Involvement of Tyrosine Kinase-2 in Both the IL-12/Th1 and IL-23/Th17 Axes. In Vivo" *J. Immunol.*, 187:181-189 (2011); Oyamada, A. et al., "Tyrosine kinase 2 plays critical roles in the pathogenic CD4 T cell responses for the development of experimental autoimmune encephalomyelitis" *J. Immunol.* 183:7539-7546 (2009)).

In humans, individuals expressing an inactive variant of Tyk2 are protected from multiple sclerosis and possibly other autoimmune disorders (Couturier, N. et al., "Tyrosine kinase 2 variant influences T lymphocyte polarization and multiple sclerosis susceptibility" *Brain* 134:693-703 (2011)). The Tyk2 rs34536443 single nucleotide polymorphism (SNP) which encodes substitution of P1104 for alanine has been found to negatively impact the function of Tyk2 and confer protection against 10 different autoimmune diseases (Dendrou, C. A. et al., "Resolving TYK2 locus genotype-to-phenotype differences in autoimmunity" *Science Transl Med* 8, 363ra149 (2016)). Moreover, data supports that the impaired cytokine signaling imparted by this SNP may be low enough to prevent autoimmunity but not severe enough to impart immunodeficiency, even in homozygous individuals. Genome-wide association studies have shown other variants of Tyk2 to be associated with autoimmune disorders such as Crohn's Disease, psoriasis, systemic lupus erythematosus, and rheumatoid arthritis, further demonstrating the importance of Tyk2 in autoimmunity (Ellinghaus, D. et al., "Combined Analysis of Genome-wide Association Studies for Crohn Disease and Psoriasis Identifies Seven Shared Susceptibility Loci"*Am. J. Hum. Genet.* 90:636-647 (2012); Graham, D. et al. "Association of polymorphisms across the tyrosine kinase gene, TYK2 in UK SLE families" *Rheumatology (Oxford)* 46:927-930 (2007); Eyre, S. et al. "High-density genetic mapping identifies new susceptibility loci for rheumatoid arthritis" *Nat. Genet.* 44:1336-1340 (2012)).

In view of the conditions that may benefit by treatment involving the modulation of cytokines and/or interferons, new compounds capable of modulating cytokines and/or interferons, such as IL-12, IL-23 and/or IFNα, and methods of using these compounds may provide substantial therapeutic benefits to a wide variety of patients in need thereof.

SUMMARY OF THE INVENTION

The invention is directed to compounds of Formula I, infra, that which are useful as modulators of IL-12, IL-23 and/or IFNα by inhibiting Tyk2-mediated signal transduction.

The present invention also provides processes and intermediates for making the compounds of the present invention.

The present invention also provides pharmaceutical compositions comprising a pharmaceutically acceptable carrier and at least one of the compounds of the present invention.

The present invention also provides a method for the modulation of IL-12, IL-23 and/or IFNα by inhibiting Tyk-2-mediated signal transduction comprising administering to a host in need of such treatment a therapeutically effective amount of at least one of the compounds of the present invention.

The present invention also provides a method for treating proliferative, metabolic, allergic, autoimmune and inflammatory diseases, comprising administering to a host in need of such treatment a therapeutically effective amount of at least one of the compounds of the present invention.

A preferred embodiment is a method for treating inflammatory and autoimmune diseases or diseases. For the purposes of this invention, an inflammatory and autoimmune disease or disorder includes any disease having an inflammatory or autoimmune component.

An alternate preferred embodiment is a method for treating metabolic diseases, including type 2 diabetes and atherosclerosis.

The present invention also provides the use of the compounds of the present invention for the manufacture of a medicament for the treatment of cancers.

The present invention also provides the compounds of the present invention for use in therapy.

These and other features of the invention will be set forth in the expanded form as the disclosure continues.

DETAILED DESCRIPTION OF THE EMBODIMENTS OF THE INVENTION

In a first aspect of the present invention, there is provided a compound of formula (I)

(I)

wherein
$R^1$ is $NH_2$ or NH $C_1$-$C_6$ alkyl;
$R^2$ is H, $C_3$-$C_{10}$ mono or bicyclic cycloalkyl or $C_1$-$C_6$ alkyl;
$R^3$ is H, $C_1$-$C_6$ alkyl, hydroxy $C_1$-$C_6$ alkyl or $C_3$-$C_8$ cycloalkyl;
$R^4$ is an 8- to 10-membered bicyclic heterocyclyl, containing 1-3 heteroatoms selected from N, O, and S, substituted with 0-4 $R^5$;
$R^5$ is H, $C_1$-$C_4$ alkyl, $C_1$-$C_4$ alkoxy, —COOH or —$CONR^6R^7$;
$R^6$ is H or $C_1$-$C_4$ alkyl;
$R^7$ is H, $C_1$-$C_4$ alkyl, $C_6$-$C_8$ aryl, hydroxy $C_1$-$C_4$ alkyl- or heterocyclyl substituted with 0-2 $R^8$; or
$R^6$ and $R^7$ are taken together with the nitrogen atom to form a 4-8 membered heterocyclyl group substituted with 0-2 $R^8$
$R^8$ is H, $C_1$-$C_4$ alkyl, halo or OH;
or a pharmaceutically acceptable salt, tautomer or stereoisomer thereof.

In a second embodiment, there is provided a compound of formula II, wherein (II)

wherein
$R^1$ is NH $C_1$-$C_6$ alkyl;
$R^2$ is $C_3$-$C_6$ cycloalkyl or $C_1$-$C_6$ alkyl;
$R^4$ is $R^5$ is H, $C_1$-$C_4$ alkyl, $C_1$-$C_4$ alkoxy, —COOH or —$CONR^6R^7$;
$R^6$ is H or $C_1$-$C_4$ alkyl;
$R^7$ is H, $C_1$-$C_4$ alkyl, $C_6$-$C_8$ aryl, hydroxy $C_1$-$C_4$ alkyl- or heterocyclyl substituted with 0-2 $R^8$; or
$R^6$ and $R^7$ are taken together with the nitrogen atom to form a 4-8 membered heterocyclyl group substituted with 0-2 $R^8$
$R^8$ is H, $C_1$-$C_4$ alkyl, halo or OH;
or a pharmaceutically acceptable salt, tautomer or stereoisomer thereof.

In a third embodiment, there is provided a compound of formula II
wherein
$R^1$ is NH $C_1$-$C_4$ alkyl;
$R^2$ is $C_3$-$C_6$ cycloalkyl or $C_1$-$C_6$ alkyl;
$R^4$ is -continued

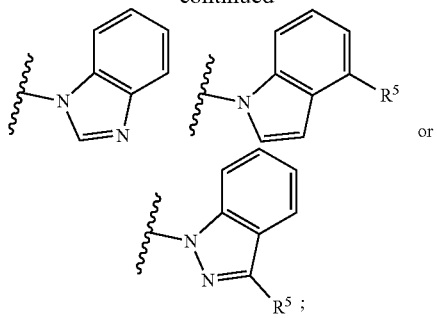

$R^5$ is H, $C_1$-$C_4$ alkyl, $C_1$-$C_4$ alkoxy, —COOH or —CONR$^6$R$^7$;
$R^6$ is H or $C_1$-$C_4$ alkyl;
$R^7$ is H, $C_1$-$C_4$ alkyl, $C_6$-$C_8$ aryl, hydroxy $C_1$-$C_4$ alkyl- or heterocyclyl substituted with 0-2 $R^8$; or
$R^6$ and $R^7$ are taken together with the nitrogen atom to form a 4-8 membered heterocyclyl group substituted with 0-2 $R^8$
$R^8$ is H, $C_1$-$C_4$ alkyl, halo or OH;
or a pharmaceutically acceptable salt, tautomer or stereoisomer thereof.

In a 4th embodiment, there is provided a compound of formula II, wherein
$R^1$ is NH $C_1$-$C_4$ alkyl;
$R^2$ is $C_3$-$C_6$ cycloalkyl;
$R^4$ is

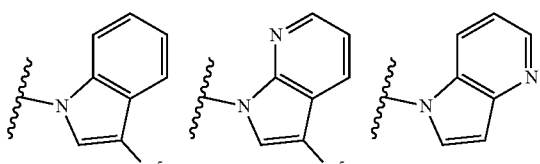

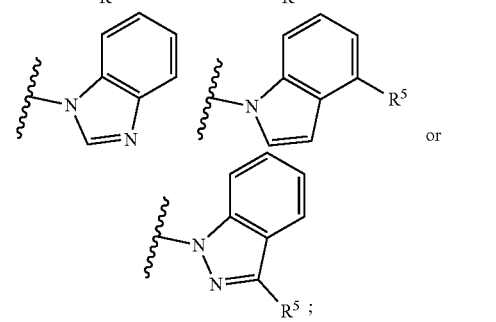

$R^5$ is H, $C_1$-$C_4$ alkyl, $C_1$-$C_4$ alkoxy, —COOH or —CONR$^6$R$^7$;
$R^6$ is H or $C_1$-$C_4$ alkyl;
$R^7$ is H, $C_1$-$C_4$ alkyl, $C_6$-$C_8$ aryl, hydroxy $C_1$-$C_4$ alkyl- or heterocyclyl substituted with 0-2 $R^8$; or
$R^6$ and $R^7$ are taken together with the nitrogen atom to form a 4-8 membered heterocyclyl group substituted with 0-2 $R^8$
$R^8$ is H, $C_1$-$C_4$ alkyl, halo or OH;
or a pharmaceutically acceptable salt, tautomer or stereoisomer thereof.

In a 5th embodiment, there is provided a compound of formula II wherein
$R^1$ is NH $C_1$-$C_4$ alkyl;
$R^2$ is $C_3$-$C_6$ cycloalkyl;
$R^4$ is

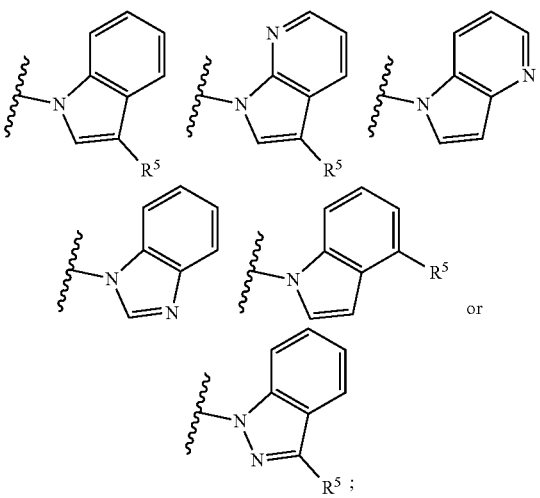

$R^5$ is H, $C_1$-$C_4$ alkyl, $C_1$-$C_4$ alkoxy, —COOH or —CONR$^6$R$^7$;
$R^6$ is H or $C_1$-$C_4$ alkyl;
$R^7$ is H, $C_1$-$C_4$ alkyl, $C_6$-$C_8$ aryl, hydroxy $C_1$-$C_4$ alkyl- or heterocyclyl substituted with 0-2 $R^8$; or
$R^6$ and $R^7$ are taken together with the nitrogen atom to form a 4-8 membered heterocyclyl group substituted with 0-2 $R^8$
$R^8$ is H, $C_1$-$C_4$ alkyl or OH;
or a pharmaceutically acceptable salt, tautomer or stereoisomer thereof.

In another embodiment, there is provided a compound of formula II,
$R^1$ is NH $C_1$-$C_4$ alkyl;
$R^2$ is $C_3$-$C_6$ cycloalkyl;
$R^4$ is

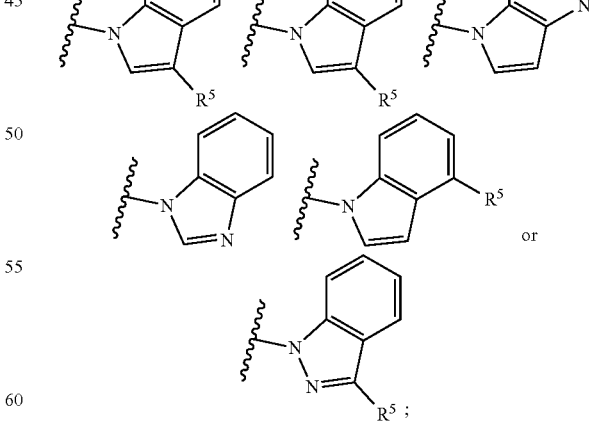

$R^5$ is H, $C_1$-$C_4$ alkyl, $C_1$-$C_4$ alkoxy, —COOH or —CONR$^6$R$^7$;
$R^6$ is H;
$R^7$ is H, $C_1$-$C_4$ alkyl, $C_6$-$C_8$ aryl, hydroxy $C_1$-$C_4$ alkyl- or heterocyclyl substituted with 0-2 $R^8$; or $R^6$ and $R^7$ are taken together with the nitrogen atom to form a 4-8 membered heterocyclyl group substituted with 0-2 $R^8$ $R^8$ is H, $C_1$-$C_4$ alkyl or OH;

or a pharmaceutically

In another embodiment, there is provided a compound of formula II wherein $R^1$ is NH $C_1$-$C_4$ alkyl;
$R^2$ is $C_3$-$C_6$ cycloalkyl;
$R^4$ is

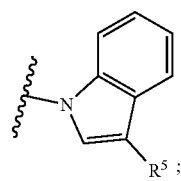

$R^5$ is H, $C_1$-$C_4$ alkyl, $C_1$-$C_4$ alkoxy, —COOH or —CONR$^6$R$^7$;

$R^6$ is H;

$R^7$ is H, $C_1$-$C_4$ alkyl, $C_6$-$C_8$ aryl, hydroxy $C_1$-$C_4$ alkyl- or heterocyclyl substituted with 0-2 $R^8$; or $R^6$ and $R^7$ are taken together with the nitrogen atom to form a 4-8 membered heterocyclyl group substituted with 0-2 $R^8$;

$R^8$ is H, $C_1$-$C_4$ alkyl or OH;

or a pharmaceutically acceptable salt, tautomer or stereoisomer thereof.

In another embodiment, there is provided a compound of formula II wherein $R^1$ is NH $C_1$-$C_4$ alkyl;
$R^2$ is $C_3$-$C_6$ cycloalkyl;
$R^4$ is

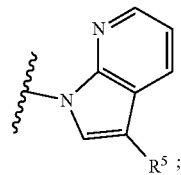

$R^5$ is H, $C_1$-$C_4$ alkyl, $C_1$-$C_4$ alkoxy, —COOH or —CONR$^6$R$^7$;

$R^6$ is H;

$R^7$ is H, $C_1$-$C_4$ alkyl, $C_6$-$C_8$ aryl, hydroxy $C_1$-$C_4$ alkyl- or heterocyclyl substituted with 0-2 $R^8$; or $R^6$ and $R^7$ are taken together with the nitrogen atom to form a 4-8 membered heterocyclyl group substituted with 0-2 $R^8$;

$R^8$ is H, $C_1$-$C_4$ alkyl or OH;

or a pharmaceutically acceptable salt, tautomer or stereoisomer thereof.

In another embodiment, there is provided a compound of formula II wherein $R^1$ is NH $C_1$-$C_4$ alkyl;
$R^2$ is $C_3$-$C_6$ cycloalkyl;
$R^4$ is

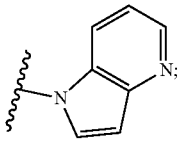

or a pharmaceutically acceptable salt, tautomer or stereoisomer thereof.

In another embodiment, there is provided a compound of formula II wherein $R^1$ is NH $C_1$-$C_4$ alkyl;
$R^2$ is $C_3$-$C_6$ cycloalkyl;
$R^4$ is

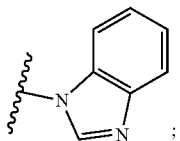 [SMILES: *n1cnc2ccccc21]

or a pharmaceutically acceptable salt, tautomer or stereoisomer thereof.

In another embodiment, there is provided a compound of formula II wherein $R^1$ is NH $C_1$-$C_4$ alkyl;
$R^2$ is $C_3$-$C_6$ cycloalkyl;
$R^4$ is

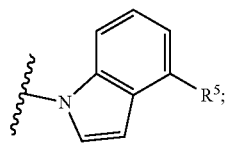

$R^5$ is H, $C_1$-$C_4$ alkyl, $C_1$-$C_4$ alkoxy, —COOH or —CONR$^6$R$^7$;

$R^6$ is H;

$R^7$ is H, $C_1$-$C_4$ alkyl, $C_6$-$C_8$ aryl, hydroxy $C_1$-$C_4$ alkyl- or heterocyclyl substituted with 0-2 $R^8$; or $R^6$ and $R^7$ are taken together with the nitrogen atom to form a 4-8 membered heterocyclyl group substituted with 0-2 $R^8$;

$R^8$ is H, $C_1$-$C_4$ alkyl or OH;

or a pharmaceutically acceptable salt, tautomer or stereoisomer thereof.

In another embodiment, there is provided a compound of formula II wherein $R^1$ is NH $C_1$-$C_4$ alkyl;
$R^2$ is $C_3$-$C_6$ cycloalkyl;
$R^4$ is

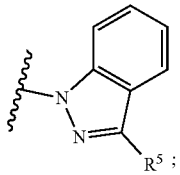

R⁵ is H, $C_1$-$C_4$ alkyl, $C_1$-$C_4$ alkoxy, —COOH or —CONR⁶R⁷;

R⁶ is H;

R⁷ is H, $C_1$-$C_4$ alkyl, $C_6$-$C_8$ aryl, hydroxy $C_1$-$C_4$ alkyl- or heterocyclyl substituted with 0-2 R⁸; or R⁶ and R⁷ are taken together with the nitrogen atom to form a 4-8 membered heterocyclyl group substituted with 0-2 R⁸;

R⁸ is H, $C_1$-$C_4$ alkyl or OH;

or a pharmaceutically acceptable salt, tautomer or stereoisomer thereof.

In another aspect, there is provided a compound selected from the exemplified examples within the scope of the first aspect, or a pharmaceutically acceptable salt, tautomer or stereoisomer thereof.

In another aspect, there is provided a compound selected from any subset list of compounds within the scope of any of the above aspects.

In another embodiment, there is provided a pharmaceutical composition comprising one or more compounds of formula (I), or stereoisomers, tautomers, pharmaceutically acceptable salts, solvates, or prodrugs thereof, and a pharmaceutically acceptable carrier or diluent.

The present invention is also directed to pharmaceutical compositions useful in treating diseases associated with the modulation of IL-12, IL-23 and/or IFNα by acting on Tyk-2 to cause signal transduction inhibition, comprising compounds of formula I, or pharmaceutically-acceptable salts thereof, and pharmaceutically-acceptable carriers or diluents.

The invention further relates to methods of treating diseases associated with the modulation of IL-12, IL-23, and/or IFNα, comprising administering to a patient in need of such treatment a therapeutically-effective amount of a compound according to formula I.

The present invention also provides processes and intermediates for making the compounds of the present invention.

The present invention also provides a method for treating proliferative, metabolic, allergic, autoimmune and inflammatory diseases (or use of the compounds of the present invention for the manufacture of a medicament for the treatment of these diseases), comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method of treating an inflammatory or autoimmune disease (or use of the compounds of the present invention for the manufacture of a medicament for the treatment of these diseases) comprising administering to a patient in need of such treatment a therapeutically-effective amount of a compound of Formula I.

The present invention also provides a method for treating a disease (or use of the compounds of the present invention for the manufacture of a medicament for the treatment of these diseases), comprising administering to a patient in need of such treatment a therapeutically-effective amount of a compound of Formula I, wherein the disease is rheumatoid arthritis, multiple sclerosis, systemic lupus erythematosus (SLE), lupus nephritis, cutaneous lupus, inflammatory bowel disease, psoriasis, Crohn's Disease, psoriatic arthritis, Sjögren's syndrome, systemic scleroderma, ulcerative colitis, Graves' disease, discoid lupus erythematosus, adult onset Stills, systemic onset juvenile idiopathic arthritis, gout, gouty arthritis, type 1 diabetes, insulin dependent diabetes mellitus, sepsis, septic shock, Shigellosis, pancreatitis (acute or chronic), glomerulonephritis, autoimmune gastritis, diabetes, autoimmune hemolytic anemia, autoimmune neutropenia, thrombocytopenia, atopic dermatitis, myasthenia gravis, pancreatitis (acute or chronic), ankylosing spondylitis, pemphigus vulgaris, Goodpasture's disease, antiphospholipid syndrome, idiopathic thrombocytopenia, ANCA-associated vasculitis, pemphigus, Kawasaki disease, Chronic Inflammatory Demyelinating Polyneuropathy (CIDP), dermatomyositis, polymyositis, uveitis, Guillain-Barre syndrome, autoimmune pulmonary inflammation, autoimmune thyroiditis, autoimmune inflammatory eye disease, and chronic demyelinating polyneuropathy.

The present invention also provides a method of treating an inflammatory or autoimmune disease (or use of the compounds of the present invention for the manufacture of a medicament for the treatment of these diseases), comprising administering to a patient in need of such treatment a therapeutically-effective amount of a compound of Formula I, wherein the disease is selected from systemic lupus erythematosus (SLE), lupus nephritis, cutaneous lupus, Crohn's Disease, ulcerative colitis, type 1 diabetes, psoriasis, rheumatoid arthritis, systemic onset juvenile idiopathic arthritis, ankylosing spondylitis, and multiple sclerosis.

The present invention also provides a method for treating a rheumatoid arthritis (or use of the compounds of the present for the manufacture of a medicament for the treatment of rheumatoid arthritis, comprising administering to a patient in need of such treatment a therapeutically-effective amount of a compound of Formula I.

In addition, the present invention also provides a method of treating a condition (or use of the compounds of the present invention for the manufacture of a medicament for the treatment of these conditions) comprising administering to a patient in need of such treatment a therapeutically-effective amount of a compound of Formula I, wherein the condition is selected from acute myelogenous leukemia, chronic myelogenous leukemia, metastatic melanoma, Kaposi's sarcoma, multiple myeloma, solid tumors, ocular neovasculization, and infantile haemangiomas, B cell lymphoma, systemic lupus erythematosus (SLE), rheumatoid arthritis, psoriatic arthritis, multiple vasculitides, idiopathic thrombocytopenic purpura (ITP), myasthenia gravis, allergic rhinitis, multiple sclerosis (MS), transplant rejection, Type I diabetes, membranous nephritis, inflammatory bowel disease, autoimmune hemolytic anemia, autoimmune thyroiditis, cold and warm agglutinin diseases, Evans syndrome, hemolytic uremic syndrome/thrombotic thrombocytopenic purpura (HUS/TTP), sarcoidosis, Sjögren's syndrome, peripheral neuropathies, pemphigus vulgaris and asthma.

The present invention also provides a method of treating a IL-12, IL-23, and/or IFNα mediated disease (or use of the compounds of the present invention for the manufacture of a medicament for the treatment of said diseases), comprising administering to a patient in need of such treatment a therapeutically-effective amount of a compound of formula I The present invention also provides a method of treating a IL-12, IL-23 and/or IFNα mediated disease (or use of the compounds of the present invention for the manufacture of a medicament for the treatment of these diseases), comprising administering to a patient in need of such treatment a therapeutically-effective amount of a compound of formula I, wherein the IL-12, IL-23 and/or IFNα mediated disease is a disease modulated by IL-12, IL-23 and/or IFNα.

The present invention also provides a method of treating diseases, comprising administering to a patient in need of such treatment a therapeutically-effective amount of a compound of formula I in combination with other therapeutic agents.

The present invention also provides the compounds of the present invention use in therapy.

In another embodiment, compounds of formula I are selected from exemplified compounds or combinations of exemplified compounds or other embodiments herein.

In another embodiment are compounds having an IC50<1000 nM in at least one of the assays described below.

The present invention may be embodied in other specific forms without departing from the spirit or essential attributes thereof. This invention encompasses all combinations of preferred aspects and/or embodiments of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

DETAILED DESCRIPTION OF THE INVENTION

The following are definitions of terms used in this specification and appended claims. The initial definition provided for a group or term herein applies to that group or term throughout the specification and claims, individually or as part of another group, unless otherwise indicated.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis and trans geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated.

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

In accordance with a convention used in the art,

is used in structural formulas herein to depict the bond that is the point of attachment of the moiety or substituent to the core or backbone structure.

A dash "-" that is not between two letters or symbols is used to indicate a point of attachment for a substituent. For example, —$CONH_2$ is attached through the carbon atom.

The term "optionally substituted" in reference to a particular moiety of the compound of Formula I (e.g., an optionally substituted heteroaryl group) refers to a moiety having 0, 1, 2, or more substituents. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "at least one chemical entity" is interchangeable with the term "a compound."

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

Alkenyl" or "alkenylene" is intended to include hydrocarbon chains of either straight or branched configuration and having one or more double carbon-carbon bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

One skilled in the field will understand that, when the designation "$CO_2$" is used herein, this is intended to refer to the group

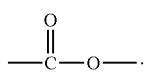

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl($C_{0-4}$)alkyl includes a substituted lower alkyl having at least one aryl substituent and also includes an aryl directly bonded to another group, i.e., aryl($C_0$)alkyl. The term "heteroarylalkyl" refers to a substituted alkyl group as defined above where at least one of the substituents is a heteroaryl.

When reference is made to a substituted alkenyl, alkynyl, alkylene, alkenylene, or alkynylene group, these groups are substituted with one to three substituents as defined above for substituted alkyl groups.

The term "alkoxy" refers to an oxygen atom substituted by alkyl or substituted alkyl, as defined herein. For example, the term "alkoxy" includes the group —O—$C_{1-6}$alkyl such as methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. "Lower alkoxy" refers to alkoxy groups having one to four carbons.

It should be understood that the selections for all groups, including for example, alkoxy, thioalkyl, and aminoalkyl, will be made by one skilled in the field to provide stable compounds.

The term "substituted", as used herein, means that any one or more hydrogens on the designated atom or group is replaced with a selection from the indicated group, provided that the designated atom's normal valence is not exceeded. When a substituent is oxo, or keto, (i.e., =O) then 2 hydrogens on the atom are replaced. Keto substituents are not present on aromatic moieties. Unless otherwise specified, substituents are named into the core structure. For example, it is to be understood that when (cycloalkyl)alkyl is listed as a possible substituent, the point of attachment of this substituent to the core structure is in the alkyl portion. Ring double bonds, as used herein, are double bonds that are formed between two adjacent ring atoms (e.g., C=C, C=N, or N=N).

Combinations of substituents and/or variables are permissible only if such combinations result in stable compounds or useful synthetic intermediates. A stable compound or stable structure is meant to imply a compound that is sufficiently robust to survive isolation from a reaction mixture to a useful degree of purity, and subsequent formulation into an efficacious therapeutic agent. It is preferred that the presently recited compounds do not contain a N-halo, $S(O)_2H$, or $S(O)H$ group.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like. As used herein, "carbocycle" or "carbocyclic residue" is intended to mean any stable 3, 4, 5, 6, or 7-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, and phenyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a bicyclic ring. When a ring is bridged, the substituents recited for the ring may also be present on the bridge.

The term "aryl" refers to monocyclic or bicyclic aromatic hydrocarbon groups having 6 to 12 carbon atoms in the ring portion, such as phenyl, and naphthyl groups, each of which may be substituted.

Accordingly, in compounds of formula I, the term "cycloalkyl" includes cyclopropyl, cyclobutyl, cyclopentyl, cyclohexyl, cycloheptyl, bicyclooctyl, etc., as well as the following ring systems:

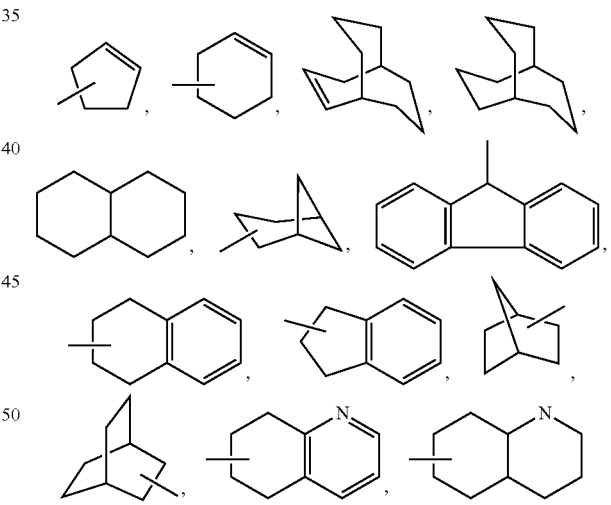

and the like, which optionally may be substituted at any available atoms of the ring(s). Preferred cycloalkyl groups include cyclopropyl, cyclopentyl, cyclohexyl, and

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes $OCF_3$.

Thus, examples of aryl groups include:

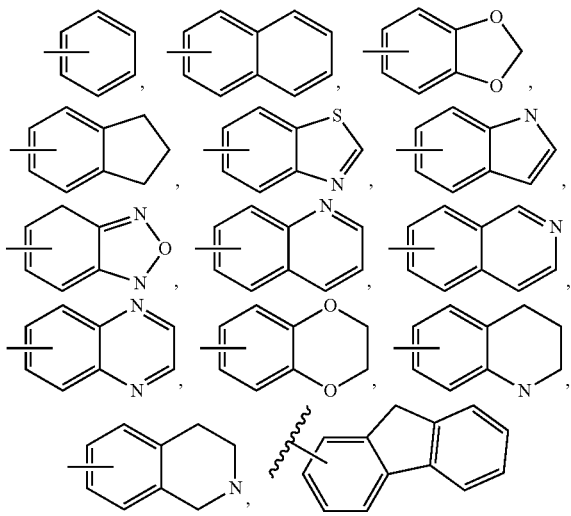

(fluorenyl) and the like, which optionally may be substituted at any available carbon or nitrogen atom. A preferred aryl group is optionally-substituted phenyl.

The terms "heterocycle", "heterocycloalkyl", "heterocyclo", "heterocyclic", or "heterocyclyl" may be used interchangeably and refer to substituted and unsubstituted 3-to 7-membered monocyclic groups, 7- to 11-membered bicyclic groups, and 10- to 15-membered tricyclic groups, in which at least one of the rings has at least one heteroatom (O, S or N), said heteroatom containing ring preferably having 1, 2, or 3 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or fully unsaturated. The heterocyclo group may be attached at any available nitrogen or carbon atom. As used herein the terms "heterocycle", "heterocycloalkyl", "heterocyclo", "heterocyclic", and "heterocyclyl" include "heteroaryl" groups, as defined below.

In addition to the heteroaryl groups described below, exemplary monocyclic heterocyclyl groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 1-pyridonyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl. Additional monocyclic heterocyclyl groups include

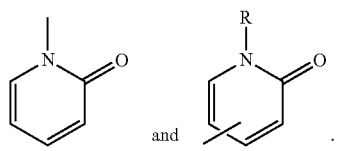

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. As valence allows, if said further ring is cycloalkyl or heterocyclo it is additionally optionally substituted with =O (oxo).

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzindolyl, phenanthrollinyl, acridinyl, phenanthridinyl, xanthenyl and the like.

In compounds of formula I, preferred heteroaryl groups include

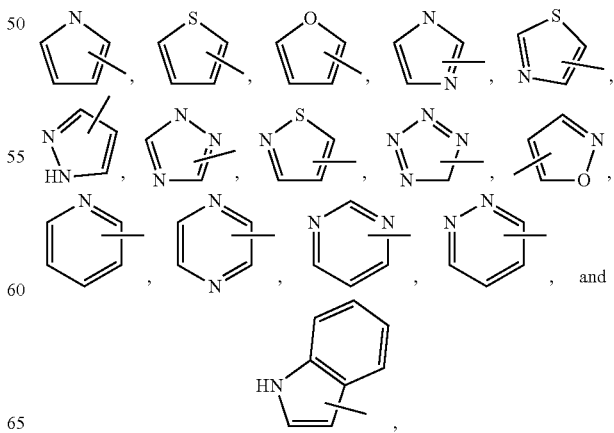

and the like, which optionally may be substituted at any available carbon or nitrogen atom.

Unless otherwise indicated, when reference is made to a specifically-named aryl (e.g., phenyl), cycloalkyl (e.g., cyclohexyl), heterocyclo (e.g., pyrrolidinyl, piperidinyl, and morpholinyl) or heteroaryl (e.g., tetrazolyl, imidazolyl, pyrazolyl, triazolyl, thiazolyl, and furyl) the reference is intended to include rings having 0 to 3, preferably 0 to 2, substituents selected from those recited above for the aryl, cycloalkyl, heterocyclo and/or heteroaryl groups, as appropriate.

The term "carbocyclyl" or "carbocyclic" refers to a saturated or unsaturated monocyclic or bicyclic ring in which all atoms of all rings are carbon. Thus, the term includes cycloalkyl and aryl rings. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of mono- and bicyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl and naphthyl. The carbocyclic ring may be substituted in which case the substituents are selected from those recited above for cycloalkyl and aryl groups.

The term "heteroatoms" shall include oxygen, sulfur and nitrogen.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The compounds of formula I may exist in a free form (with no ionization) or can form salts which are also within the scope of this invention. Unless otherwise indicated, reference to an inventive compound is understood to include reference to the free form and to salts thereof. The term "salt(s)" denotes acidic and/or basic salts formed with inorganic and/or organic acids and bases. In addition, the term "salt(s) may include zwitterions (inner salts), e.g., when a compound of formula I, contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula I may be formed, for example, by reacting a compound of the formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sci-*

*ences,* 18th Edition, Mack Publishing Company, Easton, Pa. (1990), the disclosure of which is hereby incorporated by reference.

All stereoisomers of the compounds of the instant invention are contemplated, either in admixture or in pure or substantially pure form. Stereoisomers may include compounds which are optical isomers through possession of one or more chiral atoms, as well as compounds which are optical isomers by virtue of limited rotation about one or more bonds (atropisomers). The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Prodrugs and solvates of the inventive compounds are also contemplated. The term "prodrug" denotes a compound which, upon administration to a subject, undergoes chemical conversion by metabolic or chemical processes to yield a compound of the formula I, and/or a salt and/or solvate thereof. Any compound that will be converted in vivo to provide the bioactive agent (i.e., the compound for formula I) is a prodrug within the scope and spirit of the invention. For example, compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkylbenzyl, 4-methoxybenzyl, indanyl, phthalyl, methoxymethyl, $C_{1-6}$alkanoyloxy-$C_{1-6}$alkyl, e.g., acetoxymethyl, pivaloyloxymethyl or propionyloxymethyl, $C_{1-6}$alkoxycarbonyloxy-$C_{1-6}$alkyk e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well-known physiologically hydrolyzable esters used, for example, in the penicillin and cephalosporin arts. Such esters may be prepared by conventional techniques known in the art.

Various forms of prodrugs are well known in the art. For examples of such prodrug derivatives, see:
a) Bundgaard, H., ed., *Design of Prodrugs*, Elsevier (1985), and Widder, K. et al., eds., Methods in Enzymology, 112:309-396, Academic Press (1985);
b) Bundgaard, H., Chapter 5, "Design and Application of Prodrugs", Krosgaard-Larsen, P. et al., eds., *A Textbook of Drug Design and Development,* pp. 113-191, Harwood Academic Publishers (1991); and
c) Bundgaard, H., *Adv. Drug Deliv. Rev.,* 8:1-38 (1992), each of which is incorporated herein by reference.

Compounds of the formula I and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans and cis isomers.

It should further be understood that solvates (e.g., hydrates) of the compounds of Formula I are also with the scope of the present invention. Methods of solvation are generally known in the art.

UTILITY

The compounds of the invention modulate IL-23-stimulated and IFNα-stimulated cellular functions, including gene transcription. Other types of cellular functions that may be modulated by the compounds of the instant invention include, but are not limited to, IL-12-stimulated responses.

Accordingly, compounds of formula I have utility in treating conditions associated with the modulation of the function of IL-23 or IFNα, and particularly the selective inhibition of function of IL-23, IL-12 and/or IFNα, by acting on Tyk2 to mediate signal transduction. Such conditions include IL-23-, IL-12-, or IFNα-associated diseases in which pathogenic mechanisms are mediated by these cytokines.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as modulators of IL-23-, IL-12 and IFNα-stimulated cellular responses, compounds of Formula I are useful in treating IL-23-, IL-12- or IFNα-associated diseases including, but not limited to, inflammatory diseases such as Crohn's disease, ulcerative colitis, asthma, graft versus host disease, allograft rejection, chronic obstructive pulmonary disease; autoimmune diseases such as Graves' disease, rheumatoid arthritis, systemic lupus erythematosis, cutaneous lupus, lupus nephritis, discoid lupus erythematosus, psoriasis; auto-inflammatory diseases including CAPS, TRAPS, FMF, adult onset stills, systemic onset juvenile idiopathic arthritis, gout, gouty arthritis; metabolic diseases including type 2 diabetes, atherosclerosis, myocardial infarction; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, cutaneous lupus, lupus nephritis, discoid lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoidosis, bone resorption disease, allograft rejections, fever and myalgias due to infection, cachexia secondary to infection, keloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hyposia [should this be hypoxia], vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Preferred methods of treatment are those wherein the condition is selected from Crohn's disease, ulcerative colitis, allograft rejection, rheumatoid arthritis, psoriasis, ankylosing spondylitis, psoriatic arthritis, and pemphigus vulgaris. Alternatively preferred methods of treatment are those wherein the condition is selected from ischemia reperfusion injury, including cerebral ischemia reperfusions injury arising from stroke and cardiac ischemia reperfusion injury arising from myocardial infarction. Another preferred method of treatment is one in which the condition is multiple myeloma.

When the terms "IL-23-, IL-12- and/or IFNα-associated condition" or "IL-23-, IL-12- and/or IFNα-associated disease or disorder" are used herein, each is intended to encompass all of the conditions identified above as if repeated at length, as well as any other condition that is affected by IL-23, IL-12 and/or IFNα.

The present invention thus provides methods for treating such conditions, comprising administering to a subject in need thereof a therapeutically-effective amount of at least one compound of Formula I or a salt thereof "Therapeutically effective amount" is intended to include an amount of a compound of the present invention that is effective when administered alone or in combination to inhibit IL-23, IL-12 and/or IFNα function and/or treat diseases.

The methods of treating IL-23-, IL-12 and/or IFNα-associated conditions may comprise administering compounds of Formula I alone or in combination with each other and/or other suitable therapeutic agents useful in treating such conditions. Accordingly, "therapeutically effective amount" is also intended to include an amount of the combination of compounds claimed that is effective to inhibit IL-23, IL-12 and/or IFNα function and/or treat diseases associated with IL-23, IL-12 and/or IFNα.

Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal anti-inflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); anti-malarials such as hydroxychloroquine; cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating IL-23-, IL-12- or IFNα-associated conditions by inhibiting Tyk2-mediated signal transduction, including IL-23-, IL-12- and/or IFNα-mediated diseases, as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula I and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Remington's Pharmaceutical Sciences, 17th Edition (1985), which is incorporated herein by reference in its entirety.

The compounds of Formula I may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The therapeutically-effective amount of a compound of the present invention may be determined by one of ordinary skill in the art, and includes exemplary dosage amounts for a mammal of from about 0.05 to 1000 mg/kg; 1-1000 mg/kg; 1-50 mg/kg; 5 250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species that are affected by modulation of IL-23, IL-12 and/or IFNα-mediated functions.

BIOLOGICAL ASSAYS

Probe Displacement Assay

The probe displacement assay is conducted as follows: In a 385 well plate, test compounds along with recombinantly expressed His-tagged protein corresponding to amino acids 575-869 of human Tyk2 (sequence shown below) at 2.5 nM, 40 nM ((R)—N-(1-(3-(8-methyl-5-(methylamino)-8H-imidazo[4,5-d]thiazolo[5,4-b]pyridin-2-yl)phenyl)ethyl)-2-([$^3$H]methylsulfonyl)benzamide) (preparation described below) and 80 μg/mL Copper His-Tag scintillation proximity assay beads (Perkin Elmer, Catalog #RPNQ0095) in 50 mM HEPES, pH 7.5, containing 100 μg/mL bovine serum albumin and 5% DMSO were incubated for 30 minutes at room temperature. The amount of radiolabeled probe (preparation described below) bound to Tyk2 was then quantified by scintillation counting, and the inhibition by the test compound calculated by comparison to wells either with no inhibitor (0% inhibition) or without Tyk2 (100% inhibition). The IC50 value is defined as the concentration of test compound required to inhibit radiolabeled probe binding by 50%.

Protein Sequence of recombinant Hig-tagged Tyk2 (575-869):

(SEQ ID NO: 1).
MGSSHHHHHH SSGETVRFQG HMNLSQLSFH RVDQKEITQL

SHLGQGTRTN VYEGRLRVEG SGDPEEGKMDDEDPLVPGRD

RGQELRVVLK VLDPSHHDIA LAFYETASLM SQVSHTHLAF

VHGVCVRGPE NIMVTEYVEHGPLDVWLRRE RGHVPMAWKM

```
VVAQQLASAL SYLENKNLVH GNVCGRNILL ARLGLAEGTS

PFIKLSDPGVGLGALSREER VERIPWLAPE CLPGGANSLS

TAMDKWGFGA TLLEICFDGE APLQSRSPSE

KEHFYQRQHRLPEPSCPQLA TLTSQCLTYE PTQRPSFRTI

LRDLTRL.
```

The preparation of radiolabeled probe, (R)—N-(1-(3-(8-methyl-5-(methylamino)-8H-imidazo[4,5-d]thiazolo[5,4-b]pyridin-2-yl)phenyl)ethyl)-2-([$^3$H]methylsulfonyl)benzamide, was performed as described below:

2-([$^3$H]methylsulfonyl)benzoic acid: 2-Mercaptobenzoic acid (2.3 mg, 0.015 mmol) and cesium carbonate (2 mg, 0.006 mmol) were added to a 5 mL round-bottomed flask. The flask was attached to a ported glass vacuum line and anhydrous DMF (0.5 mL) was introduced with magnetic stirring. An ampoule of tritiated methyl iodide (200 mCi, Perkin-Elmer lot 3643419) was added to the reaction flask and stirring was maintained at rt for 3 h. In-process HPLC analysis with radiometric detection indicated 80% conversion to the desired product by comparison with authentic standard. Without purification, the crude product was reacted with mCPBA (10 mg, 0.058 mmol) pre-dissolved in CH$_2$Cl$_2$ (1 mL) at room temperature with stirring. The reaction was stirred for 7 h and additional mCPBA (10 mg, 0.058 mmol) was added. The reaction was stirred for approximately 24 h and HPLC analysis indicated 35-40% conversion to the desired sulfonate product. The crude product was purified by semi-preparative HPLC (Luna Sum C$_{18}$ (10×250 cm); A: MeOH/H$_2$O=15/85 (0.1% TFA); B: MeOH; 270 nm; 0-8 min 0% B 1 ml/min; 8-10 min 0% B 1-3 ml/min; 10-55 min 0% B 3 ml/min; 55-65 min 0-10% B 3 ml/min; 65-75 min 10-50% B 3 ml/min; 75-80 min 50-100% B 3 ml/min) to give 81 mCi (40% radiochemical yield) of 2-([$^3$H]methylsulfonyl)benzoic acid product identified by its HPLC co-elution with an authentic standard. The radiochemical purity was measured by HPLC to be 99% (Luna 5u C18 (4.6×150 cm); A: H$_2$O (0.1% TFA); B: MeOH; 1.2 ml/min; 270 nm; 0-10 min 20% B; 10-15 min 20-100% B; 15-25 min 100% B. The product was dissolved in anhydrous acetonitrile to give a final solution activity of 5.8 mCi/mL. (R)—N-(1-(3-(8-methyl-5-(methylamino)-8H-imidazo[4,5-b]thiazolo[5,4-b]pyridin-2-yl)phenyl)ethyl)-2-([$^3$H]methylsulfonyl)benzamide: A solution of 2-([$^3$H]methylsulfonyl)benzoic acid (23.2 mCi) in acetonitrile was added to a 5 mL round-bottomed flask which was then attached to a vacuum line and carefully evaporated to dryness. (R)-2-(3-(1-aminoethyl)phenyl)-N,8-dimethyl-8H-imidazo[4,5-d]thiazolo[5,4-b]pyridin-5-amine (prepared as described in WO 2004/106293 and Dyckman et al., *Bioorganic and Medicinal Chemistry Letters*, 383-386 (2011)) (1.1 mg, 0.0033 mmol) and PyBOP (2 mg, 0.0053 mmol) dissolved in anhydrous DMF (1.5 mL) were added to the flask followed by N,N-diisopropylethylamine (0.010 mL). The resulting clear solution was stirred at room temperature for 18 h. HPLC analysis (Luna 5u C18 (4.6×150 cm); A: H$_2$O (0.1% TFA); B: MeOH; 1.2 ml/min; 335 nm; 0-20 min 50% B; 20-25 min 50-100% B; 25-30 min 100% B) indicated approximately a 20% conversion to the desired product by retention time comparison to a sample of non-radiolabeled (R)—N-(1-(3-(8-methyl-5-(methylamino)-8H-imidazo[4,5-d]thiazolo[5,4-b]pyridin-2-yl)phenyl)ethyl)-2-(methylsulfonyl)benzamide. The crude reaction mixture was purified by semi-preparative HPLC (Luna 5u C18 (10×250 cm); A: MeOH/H$_2$O=50/50 (0.1% TFA); B: MeOH; 335 nm; 0-40 min 0% B 3 ml/min; 40-45 min 0-100% B 3 ml/min). The purification routine was performed a second time to yield a total of 1.7 mCi (7% radiochemical yield) of the desired product in 99.9% radiochemical purity. Mass spectral analysis of the tritiated product (m/z M+H 527.33) was used to establish the specific activity at 80.6 Ci/mmol.

| Probe Displacement Data | |
|---|---|
| Example | Probe Displacement (EC50, uM) |
| 1 | 0.022 |
| 2 | 0.005 |
| 3 | 0.019 |
| 4 | 0.022 |
| 5 | 0.025 |
| 6 | 0.031 |
| 7 | 0.035 |
| 8 | 0.037 |
| 9 | 0.04 |
| 10 | 0.006 |
| 11 | 0.01 |
| 12 | 0.018 |
| 13 | 0.025 |
| 14 | 0.029 |
| 15 | 0.046 |
| 16 | 0.123 |
| 17 | 0.016 |
| 18 | 0.04 |
| 19 | 0.061 |
| 20 | 0.075 |
| 21 | 0.013 |
| 22 | 0.048 |

Kit225 T Cell Assay

Kit225 T cells with a stably-integrated STAT-dependent luciferase reporter were plated in RPMI (GIBCO) containing 10% heat-inactivated FBS (GIBCO) and 100 U/mL PenStrep (GIBCO). The cells were then stimulated with either 20 ng/mL human recombinant IL-23 or 200 U/mL human recombinant IFNα (PBL InterferonSource) for 5-6 hours. Luciferase expression was measured using the STEADY-GLO® Luciferase Assay System (PROMEGA®) according to the manufacturer's instructions. Inhibition data were calculated by comparison to no inhibitor control wells for 0% inhibition and non-stimulated control wells for 100% inhibition. Dose response curves were generated to determine the concentration required to inhibit 50% of cellular response (IC50) as derived by non-linear regression analysis.

| Kit225 T Cell Inhibition Data | | |
|---|---|---|
| Ex # | IL-23 Kit225 Reporter, (IC50, uM) | IFNa Kit225 Reporter, (IC50, uM) |
| 1 | 2.096 | 1.318 |
| 2 | 0.813 | 1.12 |
| 3 | 12.5 | 4.789 |
| 4 | 1.893 | 1.226 |
| 5 | 1.963 | 4.214 |
| 6 | 12.5 | 9.551 |
| 7 | 1.639 | 0.924 |
| 8 | 0.574 | 0.537 |
| 9 | 3.086 | 1.456 |
| 10 | 1.104 | 0.882 |
| 11 | 1.374 | 0.689 |
| 12 | 1.744 | 1.286 |
| 13 | 0.294 | 1.25 |
| 14 | 3.642 | 1.754 |
| 15 | 0.649 | 2.322 |
| 16 | 0.947 | 1.144 |

-continued

| | Kit225 T Cell Inhibition Data | |
|---|---|---|
| Ex # | IL-23 Kit225 Reporter, (IC50, uM) | IFNa Kit225 Reporter, (IC50, uM) |
| 17 | 0.355 | 0.27 |
| 18 | 0.7 | 0.511 |
| 19 | 0.511 | 0.474 |
| 20 | 0.926 | 0.475 |
| 21 | 0.661 | 0.433 |
| 22 | 12.5 | 12.5 |

METHODS OF PREPARATION

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the preparations and examples section set out hereinafter. Several of the compounds described were chiral, some were prepared as racemic mixtures, while others were prepared as a single enantiomer. In each case the preparation of the homochiral examples, or the preparation of the opposite enantiomer, may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diaststereoselectivity of transformations, providing enantio-enriched products upon cleavage of the chiral auxiliary.

Scheme 1

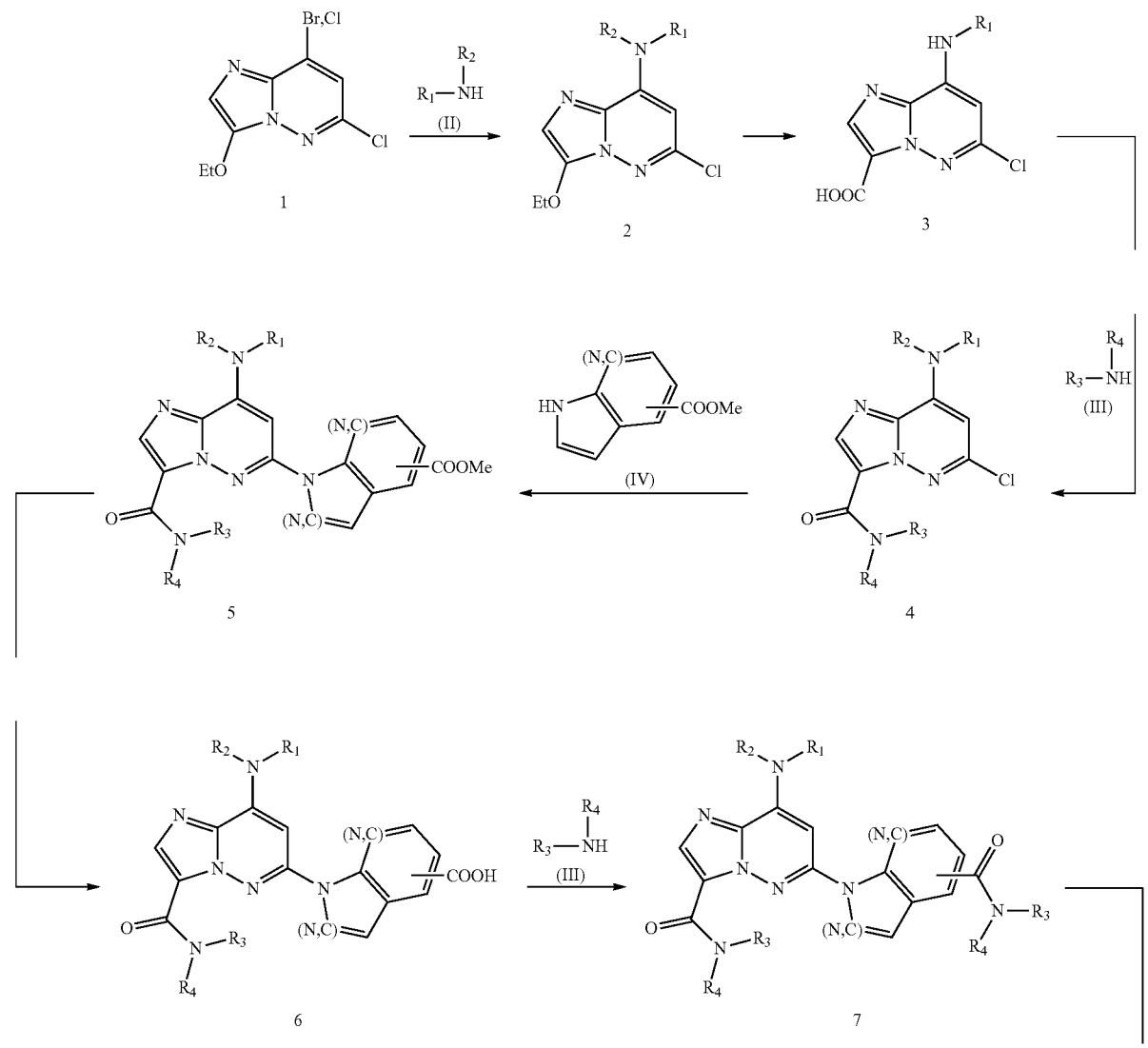

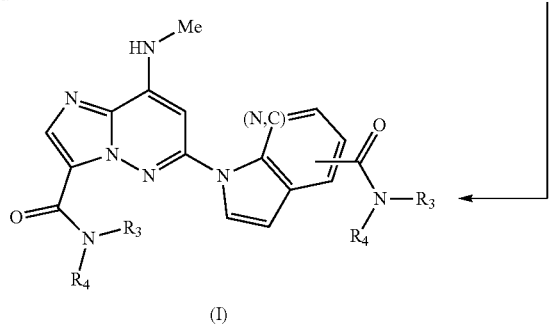

(I)

$R_1$ = aliphatic chains or cycle, $C_{6-10}$ aryl, 5-10 membered heterocycle/heteroaromatic
$R_2$ = H, removable nitrogen protecting group such as PMB
$R_3$ = substituted alphatic chains or cycles, $C_{3-10}$ cycloalkyl, 5-10 membered heterocycles, rings of the form
$R_4$ = H, rings of the form $R_3$ $R_4$ Compounds of the form (I) may be prepared via multistep synthesis initiating from 1 (prepared according to WO2010/042699) (Scheme 1).

Addition of the amine (II) may be accomplished thermally with a mild non-nucleophilic base, such as diisopropylethylamine, to provide 2.

The saponification of the ester 2 may be achieved under basic condition, such as lithium hydroxide, to provide the carboxylic acid 3.

Condensation of amine (III) with the acid 3 could be accomplished utilizing the numerous amide coupling reagents available, such as O-(7-azabenzotriazol-1-yl)-N,N,N',N'-tetramethyluronium hexafluorophosphate (HATU) or (benxotriazol-1-yloxy)tris(dimethylamino)phosphonium hexafluorophosphate (BOP), along with an appropriate base.

Addition of the amine (III) may be accomplished thermally with, or without, using a mild non-nucleophilic base, such as diisopropylethylamine.

To displace the chloro of intermediate 4 with various heterocycle (IV) alternatively palladium catalyzed N-arylation could be utilized, for which a variety of techniques are known and have been extensively reviewed (see: see Surry, D. S.; Buchwald. S. L. *Chem. Sci.* 2011, 2, 27-50 and references therein).

If the heterocycle (IV) has an ester substitution group, in most cases it can be saponified to acid using the method described above. The acid can be converted to various amides through amide coupling reaction with amine (III) using the same method described above.

If $R_2$ is a protecting group, such as para-methoxybenzene (PMB), then intermediate 7 may be converted to the target (I) using standard deprotection conditions.

In the case of PMB this includes, but is not limited to: metal catalyzed reduction—such as palladium catalyzed hydrogenation; as well as acid mediated deprotection, typically using a strong protic acid such as trifluoroacetic acid or hydrochloric acid.

Preparations

The preparations set out below are for the synthesis of reagents that were not obtained from commercial sources and were employed for the preparation of compounds of formula I of the invention. All chiral compounds in the tables and schemes are racemic unless specified otherwise.

Reverse-phase preparative high performance liquid chromatography ("HPLC") was performed with Shimadzu 8A liquid chromatographs using YMC S5 ODS columns (20× 100, 20×250, or 30×250 millimeter ("mm")). Gradient elution was performed with methanol ("MeOH")/water mixtures in the presence of 0.1% trifluoroacetic acid ("TFA").

Analytical HPLC Method Employed in Characterization of Examples

Analytical HPLC was performed on Shimadzu LC10AS liquid chromatographs using the following methods:

Method A:
Column: BEH C18 2.1×50 mm 1.7μ
Mobile Phase: Solvent A: 100% $H_2O$ w/0.05% TFA
   Solvent B: 100% ACN w/0.05% TFA
Gradient Range: 0-100% B
   Linear gradient of 0 to 100% solvent B over 1 minute
Gradient Time: ("min"), with 1.2 minute ("min") hold at 100% B.
Flow Rate: 0.8 mL/min
Analysis Time: 2.2 min
Detector: Ultraviolet ("UV") visualization at 254 nanometers ("nm")

Method B:
Column: Phenomenex 2.5μ 2.0×30 mm
Mobile Phase: Solvent A: 90% $H_2O$/10% MeOH/0.1% TFA
   Solvent B: 10% $H_2O$/90% MeOH/0.1% TFA
Gradient Range: 0-100% B
Gradient Time: 2 min
Flow Rate: 1 mL/min
Analysis Time: 3 min
Detector: UV at 254 nm Method C:
Column: Waters Acquity SDS
Mobile Phase: Solvent A: water
   Solvent B: Acetonitrile
Gradient Range: 0-100% B
Gradient Time: 1 min
Flow Rate: 0.8 mL/min
Analysis Time: 1.8 min Detector: UV at 254 nm
Method D:
Column: Waters Xbridge C18, IA CAN/AA or NH₄OH
  Solvent A: 5:95 acetonitrile:water with 10-mM
Mobile Phase:
  Solvent B: 95:5 acetonitrile:water with 10-mM NH₄OA
Gradient Range: 0-100% B
Gradient Time: 4 min
Flow Rate: 4 mL/min
Analysis Time: 5 min
Detector: UV at 220 nm
Oven Temperature: 35
Method E:
Column: Column-Asentis Express C18, 50×2.1 mm, 2.7 μm
Mobile Phase: (A) 2% acetonitrile:98% water with 10 mM NH₄COOH
  (B) 98% acetonitrile:2% water with 10 mM NH₄COOH
Gradient Range: 0-100% B
Gradient Time: 1.7 min
Flow Rate: 1 mL/min
Analysis Time: 3.2 min
Detector: UV at 220 nm
Method F:
Column: Column-Asentis Express C18, 50×2.1 mm, 2.7 μm
Mobile Phase: (A) 2% acetonitrile:98% water with 10 mM NH₄COOH
  (B) 98% acetonitrile:2% water with 10 mM NH₄COOH
Gradient Range: 0-100% B
Gradient Time: 1.5 min
Flow Rate: 1 mL/min
Analysis Time: 3.2 min
Detector: UV at 220 nm
Method G:
Column: (LCMS) Zorbax SB C18 (30×2.1 mm; 3.5 uM)
Mobile Phase: (A) buffer+acetonitrile (98:2); (B) buffer+acetonitrile (2:98)
Buffer: 10 mM Ammonium formate in water (pH 4.5)
Gradient Range: 6%-100% B (0 to 1.5 min) 100% B (to 2.2 min) 100%-6%
  B (to 2.6 min) 6% B (to 3 min)
Gradient Time: 3 min
Flow Rate: 1.5 mL/min
Analysis Time: 3 min
Detection:
Detector 1: UV at 254 nm
Detector 2: MS (ESI+)
Method H:
Column: Column: Luna C18, 4.6×30 mm, 3 μm
Mobile Phase: (A) 90:10 H₂O:MeOH TFA
  (B) 10:90 H₂O:MeOH TFA
Gradient Range: 0-100% B
Gradient Time: 5 min
Flow Rate: 4 mL/min
Analysis Time: 6 min
Detector: UV at 254 nm
Method I:
Column: Waters Sunfire C18 2.1×30 mm 3.5 μm
Mobile Phase: Solvent A: 10% methanol, 90% water, 0.1% TFA
  Solvent B: 90% methanol, 10% water, 0.1% TFA
Gradient Range: 0-100% B
Gradient Time: 4 min
Flow Rate: 1 mL/min
Analysis Time: 5 min
Oven Temperature 40
Detector: UV at 220 nm
Preparation 1

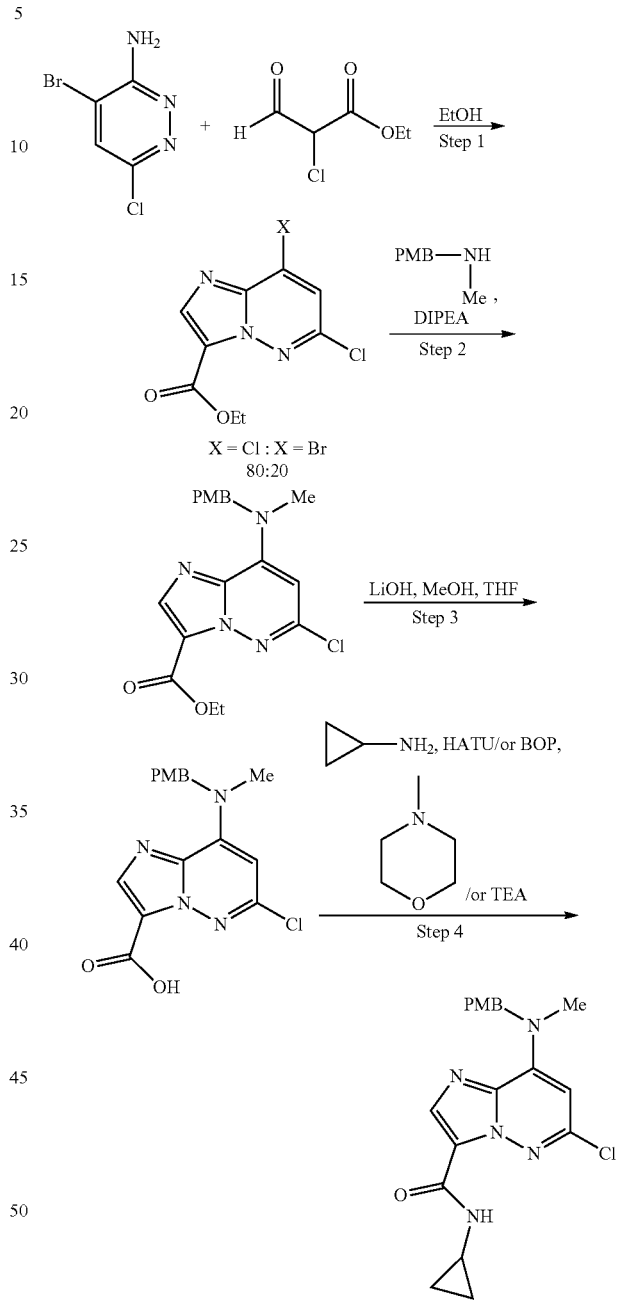

Step 1

To a solution of 4-bromo-6-chloropyridazin-3-amine (175 g, 840 mmol) in ethanol (2 L) was added ethyl 2-chloro-3-oxopropanoate (202 g, 1343 mmol) and the reaction was heated to 80° C. for 16 hours. The solvent was removed in vacuo and the residual material was diluted with water and dichloromethane. The biphasic mixture was passed through a celite bed and the filtrate was separated into two layers. The dichloromethane layer was separated and then washed with water and saturated aqueous sodium chloride (brine), it was then dried over anhydrous sodium sulfate, filtered and concentrated. The resulting crude product was purified using silica gel chromatography (0 to 20% ethyl acetate in petroleum ether). The product fractions were dried and then triturated with 10% methyl tert-butyl ether in petroleum ether (500 mL). The product was filtered off and rinsed with petroleum ether to provide the product (73 g, 33% yield) as a mixture of the C8-bromo and C8-chloro species (~80:20); the mixture was used as such in the subsequent steps (referred to as the chloride for simplicity).

$^1$H NMR (300 MHz, CDCl$_3$):

Chloro: δ 8.37 (s, 1H), 7.38 (s, 1H), 4.47 (q, J=7.2 Hz, 2H), 1.44 (t, J=7.2 Hz, 3H).

Bromo: δ 8.38 (s, 1H), 7.57 (s, 1H), 4.47 (q, J=7.2 Hz, 2H), 1.44 (t, J=7.2 Hz, 3H). LC retention time chloro: 1.04 min [G]; bromo: 1.07 [G]. Mass Spectrometry ("MS") (E+) m/z: 260 (chloro); 304 (bromo) (MH+).

Step 2

Place ethyl 6,8-dichloroimidazo[1,2-b]pyridazine-3-carboxylate (3 g, 11.54 mmol), 1-(4-methoxyphenyl)-N-methylmethanamine (2.267 g, 15.00 mmol), and N,N-Diisopropylethylamine (DIPEA) (4.03 mL, 23.07 mmol) in a 100 mL round bottle flask along with THF (15 mL). It was sealed and heated to 80° C. for 6 hours. The reaction mixture was concentrated and purified with silica gel chromatography. The product came out when eluting with 35% ethyl acetate in hexane. The fractions containing product was collected and concentrated to provide the product (3.7 g, 9.87 mmol, 86% yield, 100% purity). LC retention time 1.06 min [A]. MS (ES+) m/z: 375 (MH+).

$^1$H NMR (400 MHz, CHLOROFORM-d):

δ8.14-8.09 (m, 1H), 7.20-7.13 (m, 2H), 6.89-6.83 (m, 2H), 6.11 (s, 1H), 5.49 (s, 2H), 4.44 (q, J=7.2 Hz, 2H), 3.84-3.77 (m, 3H), 3.17 (s, 3H), 1.42 (t, J=7.2 Hz, 3H)

Step 3

Ethyl 6-chloro-8-((4-methoxybenzyl)(methyl)amino)imidazo[1,2-b]pyridazine-3-carboxylate (5.2 g, 13.87 mmol) was dissolved in THF (77 mL) and MeOH (77 mL). LiOH (41.6 mL, 125 mmol) (aq. solution) was added to the reaction mixture. After the LC-MS showed the reaction finished it was diluted with water, acidified and extracted with dichloromethane. The organic phase was dried over Na$_2$SO$_4$, filtered and concentrated to provide the crude product (4.56 g, 13.15 mmol, 95% yield, 100% purity). LC retention time 0.89 min [A]. MS (ES+) m/z: 347 (MH+).

$^1$H NMR (400 MHz, METHANOL-d$_4$):

δ8.17-8.09 (m, 1H), 7.23-7.15 (d, 2H), 6.92-6.84 (d, 2H), 6.31 (s, 1H), 5.49 (s, 2H), 3.79-3.73 (s, 3H), 3.23-3.14 (s, 3H)

Step 4

6-chloro-8-((4-methoxybenzyl)(methyl)amino)imidazo[1,2-b]pyridazine-3-carboxylic acid (0.195 g, 0.562 mmol) was added in 50 mL round flask bottle. DMF (5 mL) and N-methylmorpholine (0.309 mL, 2.81 mmol) were added to it. Cyclopropylamine was then (0.079 mL, 1.125 mmol) added to the reaction mixture. Lastly HATU (0.257 g, 0.675 mmol) was added to the reaction mixture. It was stirred at room temperature for 10 minutes. The reaction was diluted with water, extract with ethyl acetate and washed with water (×3) using brine to remove emulsions. The organic layer was dried, filtered and concentrated. The residue was purified by chromatography. The product came off the column when eluting with 45% ethyl acetate in hexane. The product fractions were collected and concentrated to give desired product (0.18 g, 0.46 mmol, 81% yield, 100% purity). LC retention time 2.18 min [B]. MS (ES+) m/z: 386 (MH+).

$^1$H NMR (400 MHz, CHLOROFORM-d):

δ8.24 (s, 1H), 7.16 (d, J=1.0 Hz, 2H), 6.86 (d, J=1.0 Hz, 2H), 6.04 (s, 1H), 5.50 (br. s., 2H), 3.81 (s, 3H), 3.22 (br. s., 3H), 3.00 (tq, J=7.3, 3.8 Hz, 1H), 0.96-0.86 (m, 2H), 0.75-0.65 (m, 2H)

Example 1

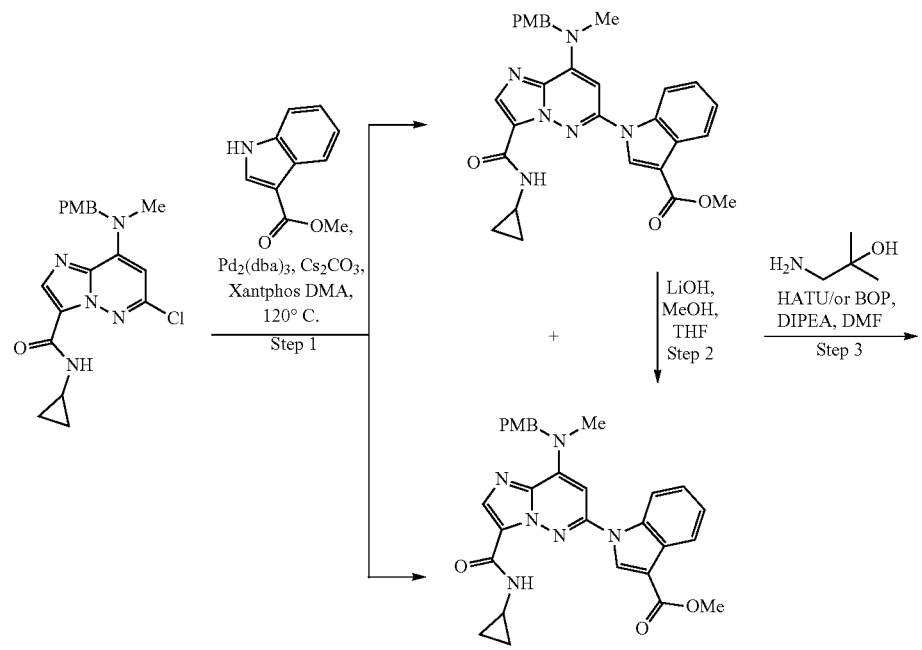

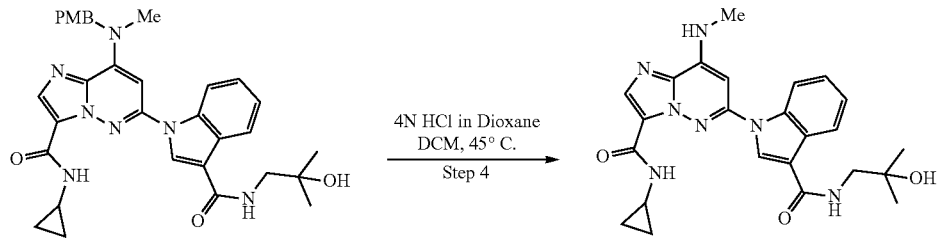

Step 1

A mixture of 6-chloro-N-cyclopropyl-8-((4-methoxybenzyl)(methyl) amino)imidazo[1,2-b]pyridazine-3-carboxamide (299 mg, 0.775 mmol), methyl 1H-indole-3-carboxylate (272 mg, 1.550 mmol), tris(dibenzylideneacetone)dipalladium(0) (Pd$_2$(dba)$_3$, 71.0 mg, 0.077 mmol), Xantphos (90 mg, 0.155 mmol) and cesium carbonate (Cs$_2$CO$_3$, 1010 mg, 3.10 mmol) in DMA (6 mL) was degassed by bubbling N$_2$ through the mixture for 5 minutes. The reaction vessel was sealed and heated to 125° C. for 90 minutes. After cooling to room temperature, the reaction mixture was partitioned between ethyl acetate (25 mL) and water (25 mL). The organic layer was washed with 10% LiCl solution (2×25 mL) and brine (25 mL). After drying (Na$_2$SO$_4$) and filtration the organic layer was concentrated to afford a purple oil that was purified using automated chromatography with a 40 g ISCO silica gel cartridge, eluting with 0-100% ethyl acetate in hexanes. The pure fractions were concentrated to afford methyl 1-(3-(cyclopropylcarbamoyl)-8-((4-methoxybenzyl)(methyl)amino)imidazo [1,2-b]pyridazin-6-yl)-1H-indole-3-carboxylate (325 mg, 0.620 mmol, 80% yield) as a brown solid. LC retention time 1.08 min [A] MS (ES+) m/z: 524 (MH+). Acid base extraction of the initial aqueous layer afforded 1-(3-(cyclopropylcarbamoyl)-8-((4-methoxybenzyl) (methyl)amino)imidazo[1,2-b]pyridazin-6-yl)-1H-indole-3-carboxylic acid (58 mg, 0.114 mmol, 14.66% yield) as a brown solid. LC retention time 0.94 min [A]. MS (ES+) m/z: 510 (MH$^+$).

Step 2

A suspension of LiOH hydrate (134 mg, 5.58 mmol) in 9 mL of water was added to a solution of methyl 1-(3-(cyclopropylcarbamoyl)-8-((4-methoxybenzyl) (methyl) amino)imidazo[1,2-b]pyridazin-6-yl)-1H-indole-3-carboxylate (325 mg, 0.620 mmol) in methanol (3 mL) and THF (3 mL) at room temperature. It was stirred at room temperature for 3 days. The reaction mixture was diluted with water (15 mL) and the pH was adjusted to <1 with 1N HCl. The mixture was extracted with dichloromethane (3×100 mL). The combined organic layers were dried over Na$_2$SO$_4$ and after filtration the organic layer was concentrated to afford 1-(3-(cyclopropylcarbamoyl)-8-((4-methoxybenzyl) (methyl)amino)imidazo[1,2-b]pyridazin-6-yl)-1H-indole-3-carboxylic acid (287 mg, 0.534 mmol, 86% yield). LC retention time 0.93 min [C]. MS (ES+) m/z: 511 (MH$^+$).

Step 3

A dichloromethane (0.5 mL) solution of 1-(3-(cyclopropylcarbamoyl)-8-((4-methoxybenzyl)(methyl)amino)imidazo[1,2-b]pyridazin-6-yl)-1H-indole-3-carboxylic acid (15 mg, 0.029 mmol), 1-amino-2-methylpropan-2-ol (7.86 mg, 0.088 mmol), N,N-Diisopropylethylamine (0.026 mL, 0.147 mmol), and HATU (16.76 mg, 0.044 mmol) was stirred at room temperature. After 15 minutes the reaction became a clear brown solution, and was complete. It was concentrated to an oil, then loaded onto a 4 g ISCO column for purification by flash chromatography, eluting with 0-100% ethyl acetate in hexanes. The reaction afforded N-cyclopropyl-6-(3-((2-hydroxy-2-methylpropyl)carbamoyl)-1H-indol-1-yl)-8-((4-methoxybenzyl)(methyl) amino)imidazo[1,2-b] pyridazine-3-carboxamide (17 mg, 0.026 mmol, 90% yield) as a white solid. LC retention time 0.92 min [A]. MS (ES+) m/z: 582 (MH+).

Step 4

To a solution of N-cyclopropyl-6-(3-((2-hydroxy-2-methylpropyl)carbamoyl)-1H-indol-1-yl)-8-((4-methoxybenzyl)(methyl)amino)imidazo[1,2-b]pyridazine-3-carboxamide (17 mg, 0.029 mmol) in dichloromethane (1 mL) was added 4N HCl in 1,4-dioxane (0.088 mL, 0.351 mmol). This solution was stirred at room temperature for 30 minutes at which point the deprotection was complete, so the reaction was concentrated to afford an oil. This was then re-dissolved in 1.5 mL DMF, filtered, and purified with preparative HPLC. The reaction afforded N-cyclopropyl-6-(3-((2-hydroxy-2-methylpropyl)carbamoyl)-1H-indol-1-yl)-8-(methylamino)imidazo[1,2-b]pyridazine-3-carboxamide (1) (4.9 mg, 10.62 μmol, 36.3% yield). LC retention time 0.73 min [C]. MS (ES+) m/z: 462 (MH$^+$).

$^1$H NMR (500 MHz, DMSO-d$_6$):

δ8.72 (s, 1H), 8.58 (d, J=4.3 Hz, 1H), 8.17 (d, J=7.9 Hz, 1H), 8.07 (s, 1H), 7.39-7.29 (m, 2H), 6.56 (s, 1H), 3.31 (d, J=6.1 Hz, 2H), 3.05 (d, J=4.3 Hz, 3H), 2.91 (td, J=7.3, 3.7 Hz, 1H), 1.16 (s, 6H), 0.78-0.70 (m, 2H), 0.57-0.48 (m, 2H)

The following compounds are prepared in a manner similar to Example 1.

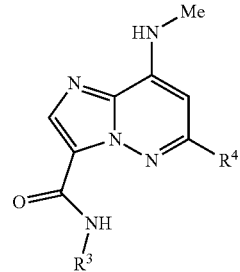

| Ex. # | R⁴ | —NHR³ | Temperature/ reaction time (hour) for step 1 | Reagent/ reaction time (hour) for step 4 | Rt (min) [Method] | m/z [M + H]+ |
|---|---|---|---|---|---|---|
| 2 | 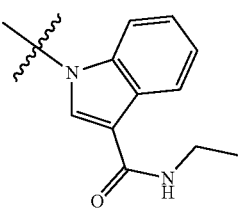 [SMILES: *n1cc(C(=O)NCC)c2ccccc21] | 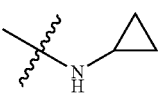 | 120° C./1.5 | 1N HCl/2 | | |
| 3 | 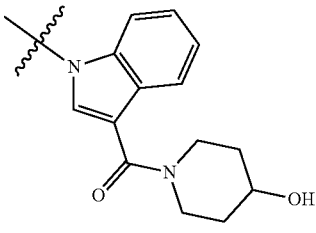 [SMILES: *n1cc(C(=O)N2CCC(O)CC2)c2ccccc21] | 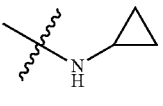 | 120° C./1.5 | 1N HCl/2 | | |
| 4 | 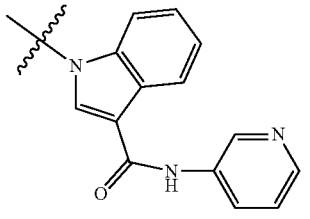 [SMILES: *n1cc(C(=O)Nc2cccnc2)c2ccccc21] | 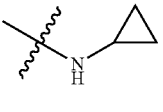 [SMILES: *NC1CC1] | 120° C./1.5 | 1N HCl/2 | | |
| 5 | 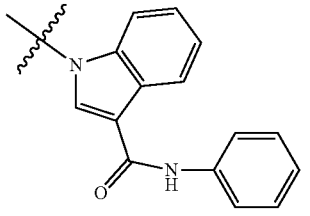 [SMILES: *n1cc(C(=O)Nc2ccccc2)c2ccccc21] | 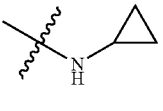 | 120° C./1.5 | 1N HCl/2 | | |
| 6 | 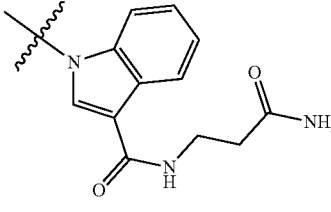 | 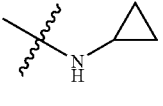 | 120° C./1.5 | 1N HCl/2 | | |
| 7 | 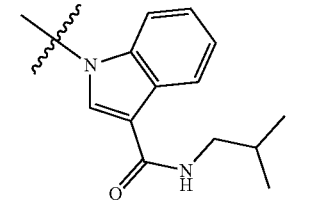 [SMILES: *n1cc(C(=O)NCC(C)C)c2ccccc21] | 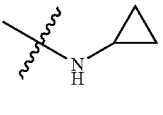 [SMILES: *NC1CC1] | 120° C./1.5 | 1N HCl/2 | | |
| 8 | 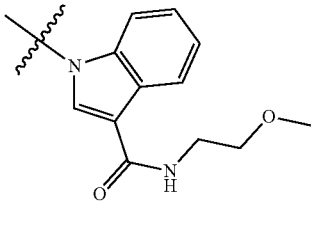 [SMILES: *n1cc(C(=O)NCCOC)c2ccccc21] | 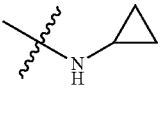 | 120° C./1.5 | 1N HCl/2 | | |

-continued

| Ex. # | R⁴ | —NHR³ | Temperature/ reaction time (hour) for step 1 | Reagent/ reaction time (hour) for step 4 | Rt (min) [Method] | m/z [M + H]+ |
|---|---|---|---|---|---|---|
| 9 | indole-3-carboxamide N-isopropyl | cyclopropylamino | 120° C./1.5 | 1N HCl/2 | | |
| 10 | indole-3-carboxamide N-(2-hydroxy-2-methylpropyl) | cyclobutylamino | 100° C./1 | 4N HCl/1 | 0.83 [A] | 476 |
| 11 | indole-3-carboxamide N-(tetrahydropyran-4-yl) | cyclobutylamino | 100° C./1 | 4N HCl/1 | 0.87 [A] | 488 |
| 12 | indole-3-morpholinocarbonyl | cyclobutylamino | 100° C./1 | 4N HCl/3 | 0.85 [A] | 474 |
| 13 | 7-azaindole-3-carboxamide N-(2-hydroxy-2-methylpropyl) | cyclopropylamino | 125° C./2 | 4N HCl/1.5 | 1.58 [D] | 463 |
| 14 | benzimidazole | cyclopropylamino | 120° C./5 | TFA/18 | 0.69 [A] | 348 |
| 15 | 4-methoxyindole | cyclopropylamino | 120° C./4.5 | 4N HCl/1.5 | 0.93 [A] | 377 |

-continued

| Ex. # | R⁴ | —NHR³ | Temperature/ reaction time (hour) for step 1 | Reagent/ reaction time (hour) for step 4 | Rt (min) [Method] | m/z [M + H]+ |
|---|---|---|---|---|---|---|
| 16 | 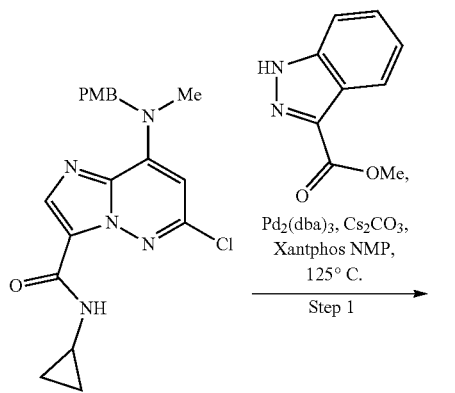 | 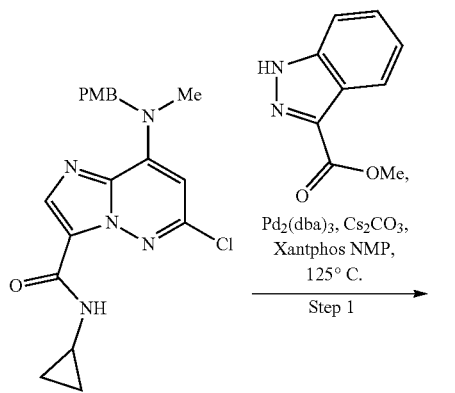 | 125° C./3 | TFA/2 | 1.82 [E] | 348 |

Example 17

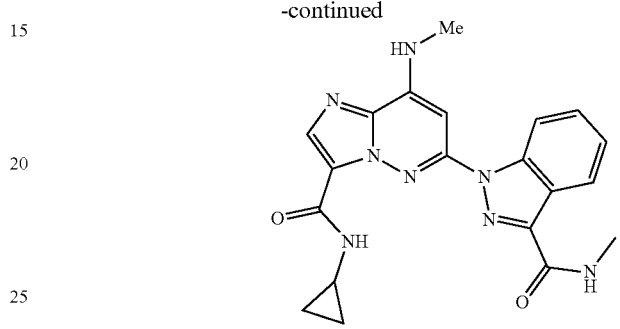

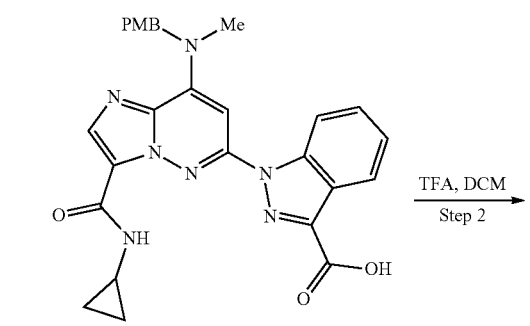

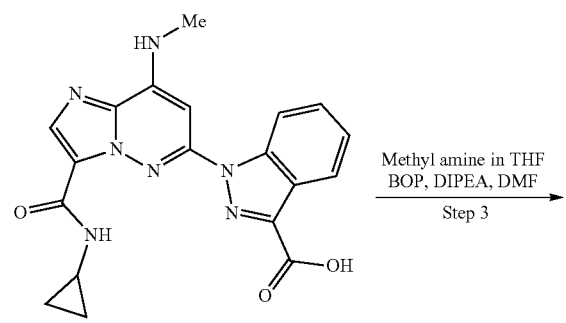

Step 1

To a stirred solution of 6-chloro-N-cyclopropyl-8-((4-methoxybenzyl)(methyl)amino)imidazo[1,2-b] pyridazine-3-carboxamide (200 mg, 0.518 mmol), methyl 1H-indazole-3-carboxylate (137 mg, 0.778 mmol), cesium carbonate (507 mg, 1.555 mmol), Pd₂(dba)₃ (47.5 mg, 0.052 mmol), and xantphos (60.0 mg, 0.104 mmol) in N-Methyl-2-pyrrolidone (NMP) (2 mL) was added under nitrogen atmosphere. It was heated at 125° C. for 3 hours, at which point conversion was determined to be about 30% by LCMS. The reaction mixture was diluted with ethyl acetate (50 mL) and filtered through a pad of celite. The filtrate was washed with water (50 mL). The aqueous layer was further extracted with ethyl acetate, the product was precipitated. It was filtered. The solid was collected and washed with ethyl acetate to get the desired 1-(3-(cyclopropylcarbamoyl)-8-((4-methoxybenzyl) (methyl)amino)imidazo[1,2-b] pyridazin-6-yl)-1H-indazole-3-carboxylic acid (90 mg, 0.163 mmol, 31.4% yield, 92.4% purity) as a yellow solid. LC retention time 1.76 min [E]. MS (ES+) m/z: 512 (MH+).

Step 2

To a stirred solution of 1-(3-(cyclopropylcarbamoyl)-8-((4-methoxybenzyl)(methyl)amino)imidazo[1,2-b] pyridazin-6-yl)-1H-indazole-3-carboxylic acid (90 mg, 0.176 mmol) in dichloromethane (2 mL) was treated with trifluoroacetic acid (TFA) (1 mL, 12.98 mmol) at room temperature. After 2 hours the reaction mixture was evaporated under vacuum and stripped off with dichloromethane (3×10 mL) and methanol (2×10 mL). The crude residue was purified by stirring with dichloromethane for 10 minutes and then the solid was filtered and collected. The solid was washed with dichloromethane to provide the desired 1-(3-(cyclopropylcarbamoyl)-8-(methylamino)imidazo[1,2-b] pyridazin-6-yl)-1H-indazole-3-carboxylic acid (80 mg, 0.186 mmol, 105% yield, 90.6% purity) as a yellow solid. LC retention time 1.68 min [E]. MS (ES+) m/z: 392 (MH+).

Step 3

A mixture of 1-(3-(cyclopropylcarbamoyl)-8-(methylamino)imidazo[1,2-b]pyridazin-6-yl)-1H-indazole-3-carboxylic acid (25 mg, 0.064 mmol), methyl amine in THF (0.064 mL, 0.128 mmol), BOP (56.5 mg, 0.128 mmol) and DIPEA (0.022 mL, 0.128 mmol) in DMF (1 mL) were stirred at room temperature for 2 hours. The reaction completed. Ethyl acetate and water were added to the reaction mixture. The aqueous layer was further extracted with ethyl acetate (3×20 mL) and the organic layer was combined, washed with brine, dried over sodium sulfate and concentrated under vacuum to dryness. The crude product was purified by preparative HPLC to get the desired N-cyclopropyl-8-(methylamino)-6-(3-(methylcarbamoyl)-1H-indazol-1-yl)imidazo[1,2-b]pyridazine-3-carboxamide (5.40 mg, 0.013 mmol, 20.86% yield, 99.8% purity) as a white solid. LC retention time 1.96 min [E]. MS (ES+) m/z: 405 (MH+).

The following compounds are prepared in a manner similar to Example 17.

Example 21

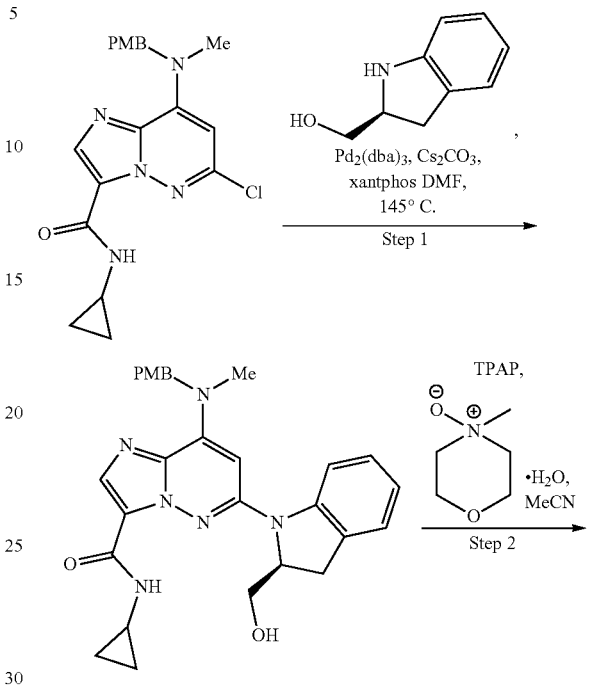

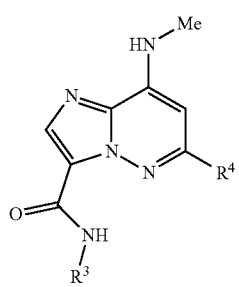

| Ex. # | R⁴ | —NHR³ | Rt (min) [Method] | m/z [M + H]+ |
|---|---|---|---|---|
| 18 | 1-(morpholine-4-carbonyl)-1H-indazol-1-yl | cyclopropylamino | 1.86 [E] | 461 |
| 19 | 3-(N,N-dimethylcarbamoyl)-1H-indazol-1-yl | cyclopropylamino | 1.98 [F] | 419 |
| 20 | 3-((2-hydroxy-2-methylpropyl)carbamoyl)-1H-indazol-1-yl | cyclopropylamino | 1.85 [E] | 463 |

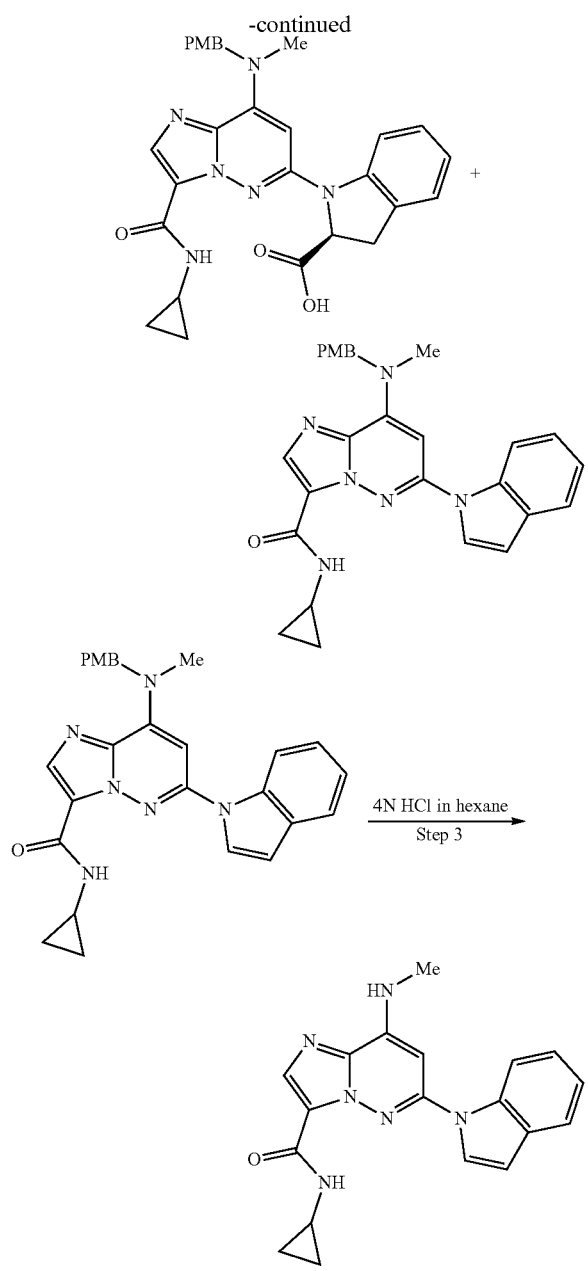

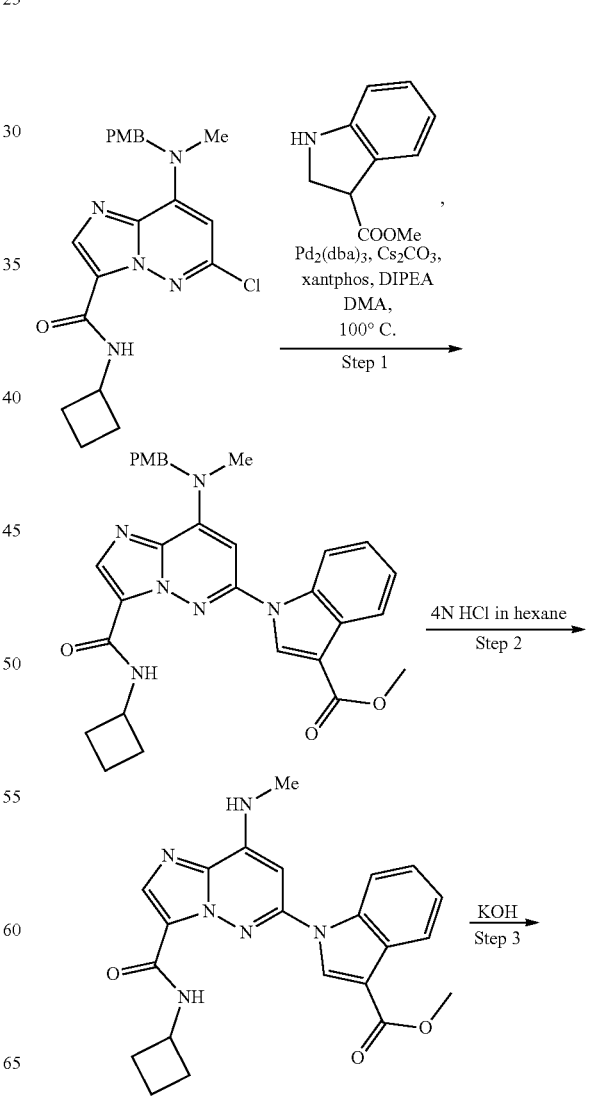

pyridazine-3-carboxamide (100 mg, 0.20 mmol) and N-methylmorpholine N-oxide monohydrate (271 mg, 2.006 mmol) were dissolved in acetonitrile (2 mL). Tetrapropylammonium perruthenate (7.05 mg, 0.020 mmol) was added and the mixture was stirred at room temperature for 12 h. The reaction was purified and provide two products, (S)-1-(3-(cyclopropylcarbamoyl)-8-((4-methoxybenzyl)(methyl)amino)imidazo[1,2-b]pyridazin-6-yl)indoline-2-carboxylic acid (21 mg, 0.041 mmol, 34% yield) and N-cyclopropyl-6-(1H-indol-1-yl)-8-((4-methoxybenzyl)(methyl)amino)imidazo[1,2-b]pyridazine-3-carboxamide (30 mg, 0.064 mmol, 53.4% yield). LC retention time 4.99 min [H]. MS (ES+) m/z: 467 (MH+).

Step 3

A solution of N-cyclopropyl-6-(1H-indol-1-yl)-8-((4-methoxybenzyl)(methyl)amino)imidazo[1,2-b]pyridazine-3-carboxamide (20 mg, 0.043 mmol) was added to HCl (0.5 mL, 2.000 mmol) (4M in dioxane). The reaction mixture was stirred at room temperature for 1 h. The reaction completed. The reaction mixture was purified by prep HPLC. (2.3 mg, 6.51 μma 15.2% yield). LC retention time 4.26 min [H]. MS (ES+) m/z: 347 (MH+).

Example 22

Step 1

To a solution of 6-chloro-N-cyclopropyl-8-((4-methoxybenzyl) (methyl)amino)imidazo[1,2-b]pyridazine-3-carboxamide (300 mg, 0.778 mmol) in DMF (1.0 mL), was added (S)-indolin-2-ylmethanol (174 mg, 1.166 mmol), Pd$_2$(dba)$_3$ (71.2 mg, 0.078 mmol), xantphos (90 mg, 0.156 mmol) and cesium carbonate (760 mg, 2.333 mmol). The reaction vial was purged with nitrogen, sealed and heated at 145° C. for 2 h. It was cooled to room temperature and water was added to the reaction. The reaction mixture was extracted with ethyl acetate (3×). The combined organic layers were washed with brine and water. The product crushed out as a yellow solid (180 mg, 0.289 mmol, 37.1% yield, >80% purity). LC retention time 0.96 min [A]. MS (ES+) m/z: 499 (MH+).

Step 2

(S)—N-cyclopropyl-6-(2-(hydroxymethyl)indolin-1-yl)-8-((4-methoxybenzyl)(methyl)amino)imidazo[1,2-b]

-continued

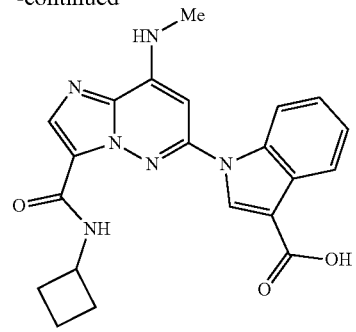

Step 1

6-chloro-N-cyclobutyl-8-((4-methoxybenzyl)(methyl)amino)imidazo[1,2-b]pyridazine-3-carboxamide (0.080 g, 0.2 mmol), (9,9-dimethyl-9H-xanthene-4,5-diyl)bis(diphenylphosphine) (0.046 g, 0.080 mmol), cesium carbonate (0.261 g, 0.800 mmol), and methyl indoline-3-carboxylate (0.071 g, 0.400 mmol) were mixed in DMA (2 mL) and degassed with nitrogen bubbling for 15 minutes. Thereafter $Pd_2(dba)_3$ (0.037 g, 0.040 mmol) was added, the mixture was degassed with nitrogen bubbling for 10 minutes and the contents were heated at 100° C. for 1 hour at which point diisopropylethylamine (DIPEA, 0.349 mL, 2.000 mmol) was added along with $Pd_2(dba)_3$ (0.037 g, 0.040 mmol). The mixture was degassed once more and heated at 100° C. for 2 hours. Water was added, the reaction mixture was carefully acidified to pH=3 with concentrated HCl, and the product was extracted into ethyl acetate (3×). The organic layers were dried (sodium sulfate) and the solvent was removed in vacuum to yield a crude product which was taken to the next step. LC retention time 1.16 min [A]. MS (ES+) m/z: 539 ($MH^+$).

Steps 2 & 3

Methyl 1-(3-(cyclobutylcarbamoyl)-8-((4-methoxybenzyl)(methyl)amino)imidazo[1,2-b]pyridazin-6-yl)-1H-indole-3-carboxylate (108 mg, 0.2 mmol) was dissolved in dichloromethane (1 mL) and HCl in dioxane (4 N) (2.500 mL, 10.00 mmol) was added to it. The contents were stirred at room temperature for 2 hours. The solvent was removed in vacuo and re-dissolved in dichloromethane and re-concentrated (×3) to remove trace of HCl. The crude product of step 2 (LC retention time 0.99 min [A]. MS (ES+) m/z: 419 ($MH^+$).) Was dissolved in methanol (2 mL) and potassium hydroxide (KOH, 5 M, 2.000 mL, 10.00 mmol) was added to the methanol solution. The mixture was stirred under nitrogen at room temperature for two days. The mixture was acidified to pH=3 and the solvent was removed in vacuum. The solvents were evaporated and the residue taken up in ethyl acetate and water. The layers were separated and the organic layer was washed once with brine, dried (sodium sulfate) and the solvent removed in vacuum to yield a brown glass. The residue was taken up in DMF and purified with preparative HPLC to give the final product (4.7 mg, 0.012 mmol, 5.81% yield, 100% purity). LC retention time 0.83 min [A]. MS (ES+) m/z: 405 ($MH^+$). 1H NMR (500 MHz, DMSO-d6) δ 8.76 (d, J=7.9 Hz, 1H), 8.64 (s, 1H), 8.30 (d, J=7.4 Hz, 1H), 8.24-8.16 (m, 2H), 8.05 (s, 1H), 7.95 (s, 1H), 7.42-7.31 (m, 2H), 6.70 (s, 1H), 4.60-4.39 (m, 1H), 3.05 (d, J=4.5 Hz, 3H), 2.34-2.20 (m, 2H), 2.01-1.82 (m, 2H), 1.77-1.58 (m, 2H)

Preparation 2

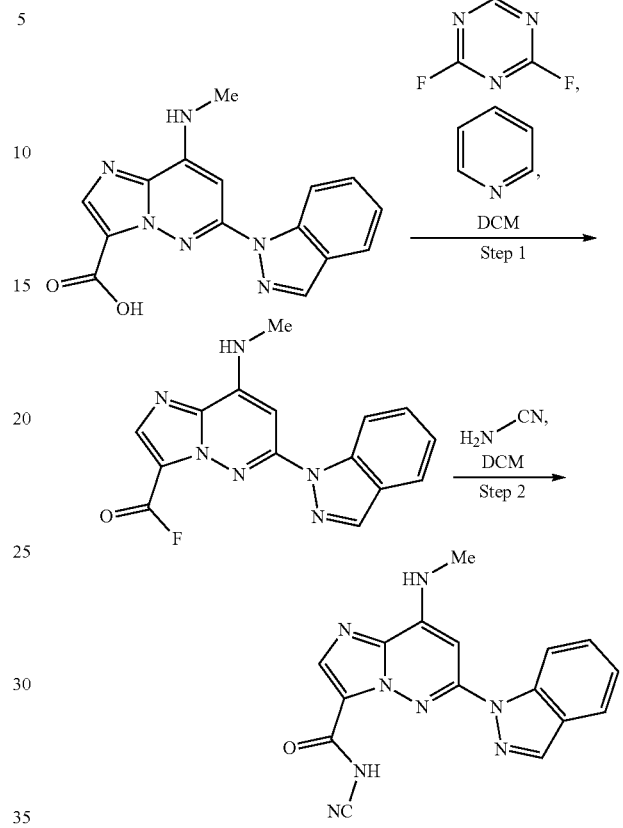

Step 1

To a solution of 6-(1H-indazol-1-yl)-8-(methylamino)imidazo[1,2-b]pyridazine-3-carboxylic acid (200 mg, 0.649 mmol) in dichloromethane (5 mL) was added 2,4,6-trifluoro-1,3,5-triazine (175 mg, 1.297 mmol) and pyridine (367 μl, 4.54 mmol). The reaction was stirred at room temperature for 2 hours to give the intermediate acyl fluoride. LC retention time 3.63 min [I]. MS (ES+) m/z: 311 ($MH^+$).

Step 2

To a solution of 6-(1H-indazol-1-yl)-8-(methylamino)imidazo[1,2-b]pyridazine-3-carbonyl fluoride (100 mg, 0.322 mmol) in dichloromethane (3 mL) was added cyanamide (67.7 mg, 1.611 mmol), and the reaction was stirred at room temperature for 16 hours. The reaction was diluted with water, and the product extracted with ethyl acetate. The organic layer was collected and concentrated to give the crude product. The crude product was purified with preparative HPLC to provide N-cyano-6-(1H-indazol-1-yl)-8-(methylamino)imidazo[1,2-b]pyridazine-3-carboxamide (1 mg, 3.01 μmol, 0.93% yield, 100% purity). LC retention time 2.93 min [I]. MS (ES+) m/z: 333 ($MH^+$).

1H NMR (500 MHz, METHANOL-$d_4$): δ9.25 (d, J=8.4 Hz, 1H), 8.22 (s, 1H), 8.02 (s, 1H), 7.77 (d, J=7.9 Hz, 1H), 7.66 (t, J=7.4 Hz, 1H), 7.30 (t, J=7.4 Hz, 1H), 7.01 (s, 1H), 3.12 (s, 3H)

NMR data for compounds in the tables:

Example 2

1H NMR (500 MHz, DMSO-$d_6$) δ8.59 (s, 1H), 8.57 (d, J=4.3 Hz, 1H), 8.27 (d, J=7.9 Hz, 1H), 8.23 (d, J=4.9 Hz,

1H), 8.19-8.15 (m, 2H), 8.07 (s, 1H), 7.39-7.27 (m, 2H), 6.54 (s, 1H), 3.34 (d, J=7.3 Hz, 2H), 3.05 (d, J=4.9 Hz, 3H), 2.91 (td, J=7.3, 4.3 Hz, 1H), 1.18 (t, J=7.3 Hz, 3H), 0.79-0.71 (m, 2H), 0.56-0.49 (m, 2H)

Example 3

$^1$H NMR (500 MHz, DMSO-$d_6$) δ8.58 (d, J=4.3 Hz, 1H), 8.33 (s, 1H), 8.21 (d, J=8.5 Hz, 1H), 8.16 (d, J=4.9 Hz, 1H), 8.06 (s, 1H), 7.72 (d, J=7.9 Hz, 1H), 7.41-7.35 (m, 1H), 7.35-7.29 (m, 1H), 6.62 (s, 1H), 4.13 (q, J=5.5 Hz, 1H), 3.35-3.28 (m, 2H), 3.17 (d, J=4.9 Hz, 2H), 3.04 (d, J=4.9 Hz, 3H), 2.94-2.89 (m, 1H), 2.73 (s, 1H), 1.79 (br. s., 2H), 1.40 (d, J=7.9 Hz, 2H), 0.80-0.72 (m, 2H), 0.58-0.51 (m, 2H)

Example 4

$^1$H NMR (500 MHz, DMSO-$d_6$) δ10.27 (s, 1H), 8.95 (d, J=1.8 Hz, 1H), 8.90 (s, 1H), 8.58 (d, J=4.3 Hz, 1H), 8.35-8.27 (m, 3H), 8.23 (t, J=7.3 Hz, 2H), 8.09 (s, 1H), 7.46-7.34 (m, 3H), 6.64 (s, 1H), 3.07 (d, J=4.9 Hz, 3H), 2.91 (dt, J=7.3, 3.7 Hz, 1H), 0.78-0.72 (m, 2H), 0.57-0.50 (m, 2H)

Example 5

$^1$H NMR (500 MHz, DMSO-$d_6$) δ10.03 (s, 1H), 8.87 (s, 1H), 8.58 (d, J=4.3 Hz, 1H), 8.31 (d, J=7.9 Hz, 1H), 8.27 (d, J=4.9 Hz, 1H), 8.21 (d, J=7.9 Hz, 1H), 8.09 (s, 1H), 7.79 (d, J=7.9 Hz, 2H), 7.42-7.34 (m, 4H), 7.09 (t, J=7.3 Hz, 1H), 6.63 (s, 1H), 3.06 (d, J=4.3 Hz, 3H), 2.92 (td, J=7.5, 4.0 Hz, 1H), 0.79-0.71 (m, 2H), 0.56-0.50 (m, 2H)

Example 6

$^1$H NMR (500 MHz, DMSO-$d_6$) δ8.63 (s, 1H), 8.56 (d, J=3.7 Hz, 1H), 8.27 (d, J=7.9 Hz, 1H), 8.22 (d, J=3.7 Hz, 2H), 8.18 (d, J=8.5 Hz, 1H), 8.07 (s, 1H), 7.41 (br. s., 1H), 7.34 (dt, J=19.8, 7.5 Hz, 2H), 6.87 (br. s., 1H), 6.53 (s, 1H), 3.50 (q, J=6.7 Hz, 2H), 3.05 (d, J=4.3 Hz, 3H), 2.95-2.90 (m, 1H), 2.41 (t, J=7.0 Hz, 2H), 0.79-0.71 (m, 2H), 0.52 (br. s., 2H)

Example 7

$^1$H NMR (500 MHz, DMSO-$d_6$) δ8.63 (s, 1H), 8.57 (d, J=4.3 Hz, 1H), 8.29-8.23 (m, 2H), 8.16 (d, J=7.3 Hz, 2H), 8.07 (s, 1H), 7.38-7.28 (m, 2H), 6.55 (s, 1H), 3.16 (d, J=5.5 Hz, 2H), 3.05 (d, J=4.9 Hz, 3H), 2.95-2.89 (m, 1H), 1.88 (dt, J=13.4, 6.7 Hz, 1H), 0.94 (d, J=6.1 Hz, 6H), 0.78-0.70 (m, 2H), 0.56-0.48 (m, 2H)

Example 8

$^1$H NMR (500 MHz, DMSO-$d_6$) δ8.65 (s, 1H), 8.57 (d, J=4.3 Hz, 1H), 8.28 (d, J=7.3 Hz, 1H), 8.24 (d, J=4.9 Hz, 2H), 8.18 (d, J=7.9 Hz, 1H), 8.07 (s, 1H), 7.40-7.29 (m, 2H), 6.53 (s, 1H), 3.51-3.47 (m, 4H), 3.30 (s, 3H), 3.05 (d, J=4.3 Hz, 3H), 2.91 (td, J=7.3, 3.7 Hz, 1H), 0.78-0.71 (m, 2H), 0.56-0.49 (m, 2H)

Example 9

$^1$H NMR (500 MHz, DMSO-$d_6$) δ8.61 (s, 1H), 8.58 (d, J=4.3 Hz, 1H), 8.27 (d, J=7.3 Hz, 1H), 8.24 (d, J=4.9 Hz, 1H), 8.15 (d, J=7.9 Hz, 1H), 8.07 (s, 1H), 7.93 (d, J=7.3 Hz, 1H), 7.39-7.28 (m, 2H), 6.55 (s, 1H), 4.20-4.14 (m, 1H), 3.05 (d, J=4.3 Hz, 3H), 2.91 (td, J=7.5, 4.0 Hz, 1H), 1.21 (d, J=6.7 Hz, 6H), 0.79-0.70 (m, 2H), 0.58-0.48 (m, 2H)

Example 10

$^1$H NMR (500 MHz, METHANOL-$d_4$) δ8.39 (s, 1H), 8.27-8.20 (m, 1H), 8.17-8.11 (m, 2H), 7.58 (s, 1H), 7.43-7.32 (m, 2H), 6.45 (s, 1H), 4.56 (quin, J=8.2 Hz, 1H), 3.47 (s, 2H), 3.15 (s, 3H), 2.43-2.29 (m, 2H), 1.99-1.87 (m, 2H), 1.79-1.65 (m, 2H), 1.29 (s, 6H)

Example 11

$^1$H NMR (500 MHz, METHANOL-$d_4$) δ8.39 (s, 1H), 8.27 (dd, J=6.4, 2.0 Hz, 1H), 8.17-8.10 (m, 2H), 7.57 (s, 2H), 7.41-7.32 (m, 2H), 6.44 (s, 1H), 4.61-4.52 (m, 1H), 4.24-4.15 (m, 1H), 4.02 (dd, J=12.1, 2.2 Hz, 2H), 3.61-3.52 (m, 2H), 3.15 (s, 3H), 2.46-2.30 (m, 2H), 2.03-1.88 (m, 4H), 1.82-1.60 (m, 4H)

Example 12

1H NMR (500 MHz, METHANOL-$d_4$) δ8.22-8.08 (m, 2H), 8.01 (s, 1H), 7.73 (d, J=7.4 Hz, 1H), 7.45-7.31 (m, 2H), 6.42 (s, 1H), 3.83-3.74 (m, 8H), 3.13 (s, 3H), 2.44-2.31 (m, 2H), 1.93 (td, J=9.3, 2.7 Hz, 2H), 1.82-1.65 (m, 3H)

Example 13

NMR miss CH3 and CH2

Example 14

$^1$H NMR (500 MHz, DMSO-$d_6$) δ9.02 (s, 1H), 8.53 (d, J=3.7 Hz, 1H), 8.22 (d, J=4.9 Hz, 1H), 8.20 (d, J=7.9 Hz, 1H), 8.06 (s, 1H), 7.82 (d, J=7.9 Hz, 1H), 7.41 (dt, J=19.8, 6.9 Hz, 2H), 6.73 (s, 1H), 3.04 (d, J=4.9 Hz, 3H), 2.92 (td, J=7.3, 3.7 Hz, 1H), 0.81-0.71 (m, 2H), 0.60-0.50 (m, 2H)

Example 15

$^1$H NMR (400 MHz, DMSO-$d_6$) δ 8.63 (d, J=4.2 Hz, 1H), 8.16 (br. s., 1H), 8.09 (s, 1H), 7.95 (d, J=3.5 Hz, 1H), 7.75 (d, J=8.4 Hz, 1H), 7.25 (t, J=8.1 Hz, 1H), 6.82 (dd, J=3.5, 0.4 Hz, 1H), 6.78 (d, J=7.9 Hz, 1H), 6.56 (s, 1H), 3.94 (s, 3H), 3.05 (br. s., 3H), 2.98-2.86 (m, 1H), 0.84-0.71 (m, 2H), 0.62-0.49 (m, 2H)

Example 16

No JDX file pdf file is available

Example 17

No JDX file pdf file is available

Example 18

No JDX file pdf file is available

Example 19

No JDX file pdf file is available

Example 20

No JDX file pdf file is available

Example 21

¹H NMR (500 MHz, METHANOL-$d_4$) δ 8.14 (s, 1H), 7.99-7.93 (m, 1H), 7.67 (d, J=7.9 Hz, 1H), 7.62 (d, J=3.5 Hz, 1H), 7.34-7.28 (m, 1H), 7.25-7.20 (m, 1H), 6.77 (d, J=3.5 Hz, 1H), 6.35 (s, 1H), 3.21-3.06 (m, 3H), 2.98-2.90 (m, 1H), 0.86-0.76 (m, 2H), 0.66-0.54 (m, 2H)

Example 22

¹H NMR (500 MHz, DMSO-$d_6$) δ 8.76 (d, J=7.9 Hz, 1H), 8.64 (s, 1H), 8.30 (d, J=7.4 Hz, 1H), 8.24-8.16 (m, 2H), 8.05 (s, 1H), 7.95 (s, 1H), 7.42-7.31 (m, 2H), 6.70 (s, 1H), 4.60-4.39 (m, 1H), 3.05 (d, J=4.5 Hz, 3H), 2.34-2.20 (m, 2H), 2.01-1.82 (m, 2H), 1.77-1.58 (m, 2H)

---

What is claimed is:

1. A compound of formula (I):

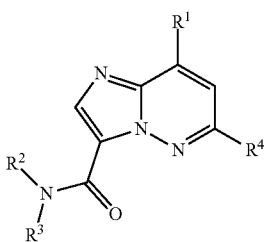

or a pharmaceutically acceptable salt, stereoisomer, or tautomer thereof,
wherein:
$R^1$ is $NH_2$ or $NHC_1$-$C_6$ alkyl;
$R^2$ is H, $C_1$-$C_6$ alkyl, or $C_3$-$C_{10}$ cycloalkyl, wherein the $C_3$-$C_{10}$ cycloalkyl is monocyclic or bicyclic;
$R^3$ is H, $C_1$-$C_6$ alkyl, $C_1$-$C_6$ alkyl-OH, or $C_3$-$C_8$ cycloalkyl;
$R^4$ is:

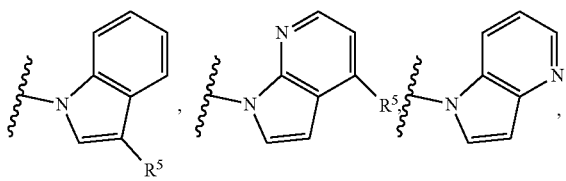

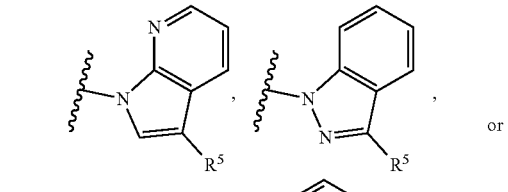

;

$R^5$ is H, $C_1$-$C_4$ alkyl, $C(O)NR^6R^7$, $C(O)OH$, or $OC_1$-$C_4$ alkyl;
$R^6$ is H or $C_1$-$C_4$ alkyl;
$R^7$ is H, $C_1$-$C_4$ alkyl, $C_1$-$C_4$ alkyl-OH, heterocyclyl, or $C_6$-$C_8$ aryl, wherein the heterocyclyl is optionally substituted with 1 or 2 independently selected $R^8$ substituents; or
$R^6$ and $R^7$, taken together with the nitrogen atom to which they are attached, form a 4- to 8-membered heterocyclyl, wherein the 4- to 8-membered heterocyclyl is optionally substituted with 1 or 2 independently selected $R^8$ substituents; and each $R^8$ is independently H, halo, $C_1$-$C_4$ alkyl, or OH.

2. The compound according to claim 1, or a pharmaceutically acceptable salt, stereoisomer, or tautomer thereof, wherein $R^1$ is $NHC_1$-$C_4$ alkyl.

3. The compound according to claim 2, or a pharmaceutically acceptable salt, stereoisomer, or tautomer thereof, wherein $R^2$ is $C_3$-$C_6$ cycloalkyl, wherein the $C_3$-$C_6$ cycloalkyl is monocyclic or bicyclic.

4. The compound according to claim 3, or a pharmaceutically acceptable salt, stereoisomer, or tautomer thereof, wherein each $R^8$ is independently H, $C_1$-$C_4$ alkyl, or OH.

5. The compound according to claim 4, or a pharmaceutically acceptable salt, stereoisomer, or tautomer thereof, wherein:

$R^6$ is H; and
$R^7$ is H, $C_1$-$C_4$ alkyl, $C_1$-$C_4$ alkyl-OH, heterocyclyl, or $C_6$-$C_8$ aryl, wherein the heterocyclyl is optionally substituted with 1 or 2 independently selected $R^8$ substituents; or
$R^6$ and $R^7$, taken together with the nitrogen atom to which they are attached, form a 4- to 8-membered heterocyclyl, wherein the 4- to 8-membered heterocyclyl is optionally substituted with 1 or 2 independently selected $R^8$ substituents.

6. The compound according to claim 5, or a pharmaceutically acceptable salt, stereoisomer, or tautomer thereof, wherein $R^4$ is:

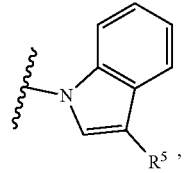

7. The compound according to claim 5, or a pharmaceutically acceptable salt, stereoisomer, or tautomer thereof, wherein $R^4$ is:

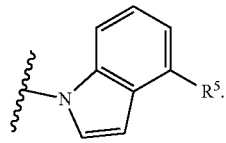

8. The compound according to claim 5, or a pharmaceutically acceptable salt, stereoisomer, or tautomer thereof, wherein $R^4$ is:

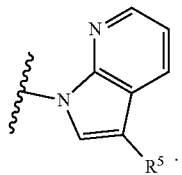

9. The compound according to claim 5, or a pharmaceutically acceptable salt, stereoisomer, or tautomer thereof, wherein $R^4$ is:

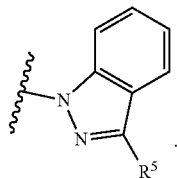

10. The compound according to claim 1, or a pharmaceutically acceptable salt, stereoisomer, or tautomer thereof, wherein $R^4$ is:

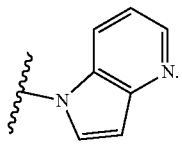

11. The compound according to claim 1, or a pharmaceutically acceptable salt, stereoisomer, or tautomer thereof, wherein $R^4$ is:

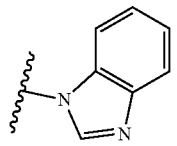

12. A pharmaceutical composition comprising a pharmaceutically acceptable carrier or diluent and at least one compound according to claim 1, or a pharmaceutically acceptable salt, stereoisomer, or tautomer thereof.

13. A method for modulating interleukin-23 activity or interferon-alpha activity in a patient, wherein the method comprises administering to the patient in need of such treatment a therapeutically effective amount of at least one compound according to claim 1, or a pharmaceutically acceptable salt, stereoisomer, or tautomer thereof.

14. The method according to claim 13, wherein the patient has an autoimmune disease or an inflammatory disease.

15. The method according to claim 14, wherein the autoimmune disease or the inflammatory disease is selected from the group consisting of acute myelogenous leukemia, acute pancreatitis, acute synovitis, adult respiratory distress syndrome, Alzheimer's disease, an allergy, an allograft rejection, an angiogenic disorder, asthma, atherosclerosis, atopic dermatitis, autoimmune gastritis, autoimmune hemolytic anemia, autoimmune neutropenia, bone resorption disease, cachexia, cardiac hypertrophy, cardiac reperfusion injury, cerebral ischemia, cerebral malaria, chronic active hepatitis, chronic myelogenous leukemia, chronic obstructive pulmonary disease, chronic pancreatitis, chronic pulmonary inflammatory disease, chronic thyroiditis, a condition associated with prostaglandin endoperoxidase synthase-2, Crohn's disease, cutaneous lupus, diabetes, discoid lupus erythematosus, a disease characterized by massive neutrophil infiltration, endotoxemia fever due to infection, glomerulonephritis, gout, gouty arthritis, graft versus host disease, Graves' disease, inflammatory bowel disease, an inflammatory reaction induced by an endotoxin, influenza, an ischemia in heart attack, an ischemia in stroke, Kaposi's sarcoma, keloid formation, lupus nephritis, metastatic melanoma, multiple myeloma, multiple sclerosis, muscle degeneration, a myalgia due to infection, myasthenia gravis, myocardial ischemia, a neurodegenerative disease caused by traumatic injury, organ hypoxia, osteoarthritis, osteoporosis, pancreatic B-cell disease, Parkinson's disease, pemphigus vulgaris, psoriasis, psoriatic arthritis, pulmonary sarcoidosis, pyresis, Reiter's syndrome, renal reperfusion injury, rheumatoid arthritis, rheumatoid spondylitis, rubella arthritis, scar tissue formation, scleroderma, sepsis, septic shock, shigellosis, silicosis, stroke, systemic lupus erythematosis, thrombin-induced platelet aggregation, thrombocytopenia, thrombosis, toxic shock syndrome, traumatic arthritis, tuberculosis, ulcerative colitis, vascular hyperplasia, and a viral disease.

16. The method according to claim 15, wherein the angiogenic disorder is an ocular neovasculization, an infantile hemangioma, or a solid tumor.

17. The method according to claim 15, wherein the cachexia is cachexia secondary to infection.

18. The method according to claim 15, wherein the viral disease is an acute hepatitis infection, anthrogryposis-renal dysfunction-cholestasis syndrome, cytomegalovirus retinitis, herpes, or a human immunodeficiency virus infection.

19. The method according to claim 18, wherein the acute hepatitis infection is hepatitis A, hepatitis B, or hepatitis C.

20. The method according to claim 18, wherein the human immunodeficiency virus infection is acquired immunodeficiency syndrome.

* * * * *

SEQUENCE LISTING

<160> NUMBER OF SEQ ID NOS: 1

<210> SEQ ID NO 1
<211> LENGTH: 317
<212> TYPE: PRT
<213> ORGANISM: Homo sapiens

<400> SEQUENCE: 1

```
Met Gly Ser Ser His His His His His His Ser Ser Gly Glu Thr Val
 1               5                  10                  15

Arg Phe Gln Gly His Met Asn Leu Ser Gln Leu Ser Phe His Arg Val
            20                  25                  30

Asp Gln Lys Glu Ile Thr Gln Leu Ser His Leu Gly Gln Gly Thr Arg
        35                  40                  45

Thr Asn Val Tyr Glu Gly Arg Leu Arg Val Glu Gly Ser Gly Asp Pro
    50                  55                  60

Glu Glu Gly Lys Met Asp Asp Glu Asp Pro Leu Val Pro Gly Arg Asp
65                  70                  75                  80

Arg Gly Gln Glu Leu Arg Val Val Leu Lys Val Leu Asp Pro Ser His
                85                  90                  95

His Asp Ile Ala Leu Ala Phe Tyr Glu Thr Ala Ser Leu Met Ser Gln
            100                 105                 110

Val Ser His Thr His Leu Ala Phe Val His Gly Val Cys Val Arg Gly
        115                 120                 125

Pro Glu Asn Ile Met Val Thr Glu Tyr Val Glu His Gly Pro Leu Asp
    130                 135                 140

Val Trp Leu Arg Arg Glu Arg Gly His Val Pro Met Ala Trp Lys Met
145                 150                 155                 160

Val Val Ala Gln Gln Leu Ala Ser Ala Leu Ser Tyr Leu Glu Asn Lys
                165                 170                 175

Asn Leu Val His Gly Asn Val Cys Gly Arg Asn Ile Leu Leu Ala Arg
            180                 185                 190

Leu Gly Leu Ala Glu Gly Thr Ser Pro Phe Ile Lys Leu Ser Asp Pro
        195                 200                 205

Gly Val Gly Leu Gly Ala Leu Ser Arg Glu Glu Arg Val Glu Arg Ile
    210                 215                 220

Pro Trp Leu Ala Pro Glu Cys Leu Pro Gly Gly Ala Asn Ser Leu Ser
225                 230                 235                 240

Thr Ala Met Asp Lys Trp Gly Phe Gly Ala Thr Leu Leu Glu Ile Cys
                245                 250                 255

Phe Asp Gly Glu Ala Pro Leu Gln Ser Arg Ser Pro Ser Glu Lys Glu
            260                 265                 270

His Phe Tyr Gln Arg Gln His Arg Leu Pro Glu Pro Ser Cys Pro Gln
        275                 280                 285
```

```
Leu Ala Thr Leu Thr Ser Gln Cys Leu Thr Tyr Glu Pro Thr Gln Arg
    290             295             300
Pro Ser Phe Arg Thr Ile Leu Arg Asp Leu Thr Arg Leu
305             310             315
```